Figure 1:
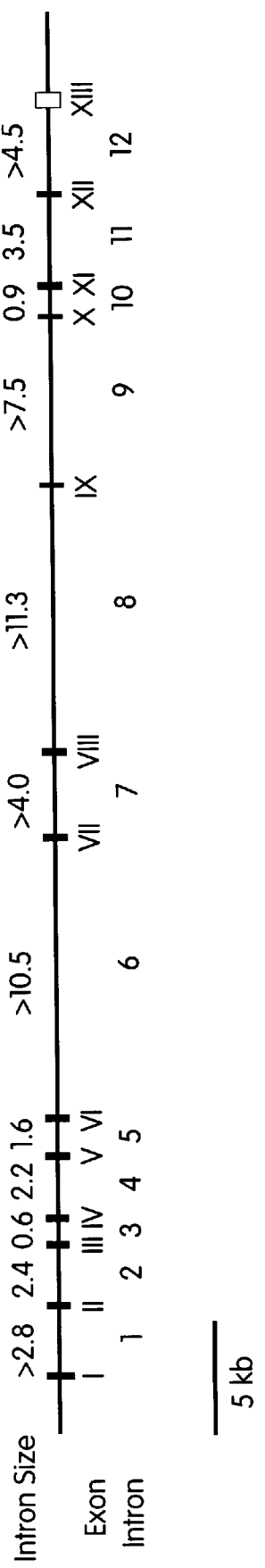

United States Patent [19]
Acton et al.

[11] Patent Number: 6,030,778
[45] Date of Patent: Feb. 29, 2000

[54] DIAGNOSTIC ASSAYS AND KITS FOR BODY MASS DISORDERS ASSOCIATED WITH A POLYMORPHISM IN AN INTRON SEQUENCE OF THE SR-BI GENE

[75] Inventors: Susan Laurene Acton, Lexington; Jose M. Ordovas, Framingham, both of Mass.

[73] Assignee: Millennium Pharmaceuticals, Inc., Cambridge, Mass.

[21] Appl. No.: 08/890,979

[22] Filed: Jul. 10, 1997

[51] Int. Cl.⁷ .............................. C12Q 1/68; C12P 19/34; C07H 21/04

[52] U.S. Cl. .................. 435/6; 435/91.2; 536/24.31; 536/24.33

[58] Field of Search ....................... 435/6, 91.2; 536/23.5

[56] References Cited

U.S. PATENT DOCUMENTS

4,683,195   7/1987   Mullis et al. ............................ 435/91.2

FOREIGN PATENT DOCUMENTS

| | | |
|---|---|---|
| WO 96/00288 | 1/1996 | WIPO . |
| WO 97/02048 | 1/1997 | WIPO . |
| WO 97/18304 | 5/1997 | WIPO . |
| WO 98/39431 | 9/1998 | WIPO . |

OTHER PUBLICATIONS

Orita, M. et al. "Detection of Polymorphisms of Human DNA by Gel Electrophoresis as Single–Strand Conformation Polymorphisms" *PNAS* 86(8):2766–2770, Apr. 1989, XP000310584.

Saiki, R.K. et al. "Genetic Analysis of Amplified DNA with Immobilized Sequence–Specific Oligonucleotide Probes" *PNAS* 86(16):6230–6234, Aug. 1989, XP000268602.

Frossard, P.M. et al. "ApaI RFLP 5.4 kn 5' to the human apolipoprotein AI (APO A1) gene" *Nuc. Acids Res.* 14(4), 1986, XP002090828.

International Search Report for PCT/US98/14354 dated Feb. 4, 1999.

Hillier, L. et al. "The WashU–Merck EST project (AC H22816)" EMEST13, 1995, XP002095407, Heidelberg.

Hillier, L. et al. "The WashU–Merck EST project (AC T39475)" EMEST13, 1995, XP002095408, Heidelberg.

Hillier, L. et al. "The WashU–Merck EST project (AC R59536)" EMEST13, 1995, XP002095409, Heidelberg.

Sanger, F. et al. "DNA Sequencing with Chain–Terminating Inhibitors" *PNAS*, 74(12):5463–5467, Dec. 1977, XP000604551.

Botstein, D. et al. "Construction of a Genetic Linkage Map in Man Using Restriction Fragment Length Polymorphisms" *Am. J. Hum. Gen.* 32(3):314–331, May 1980, XP000610566.

Nickerson, D. et al. "Automated DNA Diagnostics Using an ELISA–Based Oligonucleotide Ligation Assay" *PNAS* 87(22):8923–8927, Nov. 1990, XP000209335.

Ganguly, A. et al. "Detection of Single–Based Mutations by Reaction of DNA Heteroduplexes with a Water–Soluble Carbodiimide Followed by Primer Extension: Application to Products from the Polymerase Chain Reaction" *Nuc. Acids Res.* 18(13):3933–3939, 1990, XP002033171.

Acton, S.L. et al. "Expression Cloning of SR–BI, a CD36–related Class B Scavenger Receptor" *J. Biol. Chem.* 269 (33):21003–21009, 1994.

Acton, S. et al. "Identification of Scavenger Receptor SR–BI as a High Density Lipoprotein Receptor" *Science* 271:518–520, 1996.

Calvo, D. and Vega, M.A. "Identification, primary structure, and distribution of CLA–1, a novel member of the CD36/LIMPH gene family" *J. Biol. Chem.* 268 (25):18929–18935, 1993.

Calvo, D. et al. "The CD36, CLA–1 (CD36L1), and LIMPII (CD36L2) Gene Family: Cellular Distribution, Chromosomal Location, and Genetic Evolution" *Genomics* 25:100–106, 1995.

Fukasawa, M. et al. "SRB1, a Class B scavenger receptor, recognizes both negatively charged liposomes and apoptotic cells" *Exper. Cell Research* 222:246–250, 1996.

Rigotti, A. et al. "The Class B Scavenger Receptors SR–BI and CD36 are Receptors for Anionic Phospholipids" *J. Biol. Chem.* 270 (27):16221–16224, 1995.

Tang, Y. et al. "Identification of a Human CD36 Isoform Produced by Exon Skipping" *J. Biol. Chem* 269 (8):6011–6015, 1994.

Wang, N. et al. "Scavenger Receptor BI (SR–BI) is up–regaulated in adrenal gland in apolipoprotein A–I and hepatic lipase knock–out mice as a response to depletion of cholesterol stores" *J. Biol. Chem* 271 (35):21001–21004, 1996.

Varban et al. P.N.A.S. (Apr. 1998) 95: 4619–4624.

Rigotti et al. P.N.A.S. (Nov. 1997) 94: 12610–12615.

*Primary Examiner*—Lisa B. Arthur
*Attorney, Agent, or Firm*—Foley, Hoag & Eliot LLC; Beth E. Arnold, Esq.; Isabelle M. Clauss

[57] ABSTRACT

The present invention is based at least in part on the discovery of a polymorphism in the human SR-BI gene which is genetically linked with a high body mass index. Accordingly, the invention provides diagnostic assays and kits for determining whether a subject has or is at risk of developing an abnormal body mass index, such as a high body mass.

28 Claims, 12 Drawing Sheets promoter and exon 1

ACTGCGGAGATGAGGGTCTAGAAGGTGGTGGCGGGGCAT
GTGGACCGTTGTAAGGGCTCTGGGGTTCCTGGGTGGGCT
GGCGAAGTCCTACTCACAGTGACCAACCATGATGATGGT
CCCGATAGAGGAGGAGAGGGAGGAGGAGGGAAAAGGAAG
GGTGAGGGGCTCAGAGGGGAGAGCTGGGAGGAGGGGAGA
CATAGGTGGGGGAAGGGGTAGGAGAAAGGGGAAGGGAGC
AAGAGGGTGAGGGGCACCAGGCCCATAGACGTTTTGGC
TCAGCGGCCACGAGGCTTCATCAGCTCCCGCCCGAAAAC
GGAAGCGAGGCCGTGGGGCAGCGGCAGCATGGCGGGGC
TTGTCTTGGCGGCCATGGCCCCGCCCCTGCCCGTCCGA
TCAGCGCCCCGCCCCGTCCCCGCCCCGACCCCGCCCGG
GCCCGCTCAGGCCCCGCCCCTGCCGCCGGAATCCTGAAG
CCCAAGGCTGCCGGGGGCGGTCCGGCGGCCGGCGAT
GGGGC*ATAAAA*CCACTGGCCACCTGCCGGGCTGCTCC

*TGCGTGCGCTGCCGTCCCGGATCC*ACCGTGCCTCTGCGG
CCTGCGTGCCCGGAGTCCCCGCCTGTGTCGTCTCTGTCG
CCGTCCCCGTCTCCTGCCAGGCGCGGAGCCCTGCGAGCC
GCGGGTGGGCCCCAGGCGCGCAGACATGAGCTGCTCCGC
CAAAGCGCGCTGGGCTGCCGGGGCGCTGGGCGTCGCGGG
GCTACTGTGCGCTGTGCTGGGCGCTGTCATGATCGTGAT
GGTGCCGTCGCTCATCAAGCAGCAGGTCCTTAAG

GTGGGTGAGGGAGACCCAGGGGGTCCGCGCACGGACCC
GGGCTGTTGGGCGCTGGGCGCCGGGAGGACCCGCGCGTT
GCGGTGGGTGGGCGACCGCAGCGGAATCGGCGCCCGGGC
CTGGCGCCGCAGAACACGAGGGAGGCCAGGCGCTTCGGG
AGGGGCTGCTGCCCGCCTCCCACCACCCTCACC

Fig. 2A exon 2

AGCCTCATGTGCGAAGGGCTTTCCCACCACCTCCTATCC
CAAGCTCCCGCCGAGGAGCCCCTTCCCTGGCCGGGCTCG
GGCAGCTGTTCCGGAGCCTTGTGGTGGGGCG**TGGGGCC
CTCATCACTCTCCTCA**CAAGCGTACTTGTCCCTTCCC
CTGCAG

<u>AACGTGCGCATCGACCCCAGTAGCCTGTCCTTCAACATG
TGGAAGGAGATCCCTATCCCCTTCTATCTCTCCGTCTAC
TTCTTTGACGTCATGAACCCAGCGAGATCCTGAAGGGC
GAGAAGCCGCAGGTGCGGGAGCGCGGGCCCTACGTGTAC
AG</u>

GTGAGGCTGTGTCCACGTGATGGTGGACGGGCCGGCTGA
CGCTGGGCATGGACGGGTCTCAN**AGTGGACGGGATG
GGGAGGCTGC**TGACTGACCCCCAAACATTGTTCCGGAA
GCACGCAACTCATAGTCGGGGTAAGTGCTACTCCCAAAA
AAGTTTGCGT exon 3

CATGTCCTGCAGTGGGCAGGCAGCGGGAGGGACAGACTT
GGCGAAGGGGCCGAGCTCAGCTTTGGCTGTGGGGCCGGA
GGTGTGCACAGACGTCCAGGGCCCTGGTTCCCAGGCAG
GCATTGCAGGCGAGTAGAAGGGAAACGTCCATGCAG
CGGGGCGGGGCGTCTGACCCACTGGCTTCCCCCACAG

<u>GGAGTTCAGGCACAAAAGCAACATCACCTTCAACAACAA
CGACACCGTGTCCTTCCTcGAGTACCGCACCTTCCAGTT
CCAGCCCTCCAAGTCCACGGCTCGGAGAGCGACTACAT
CATCATGCCCAACATCCTGGTCTTG</u>

GTGAGGCTGCCCTGTGGCCCACGCCGCCTCGCACCCTGA
CCTCGTCCCCTGTCTCTCCTCCCGCCTGCCCTTGTG
CAGAGAGCAGTCCCTGAGGTGGTCGGAGCGTGGGGACTC
ACGCCTGGTGGGTGGCTTTCGGCCCTGTGCTGTCTCCAC
CACCCCCA

Fig. 2B exon 4

GGTGGTTCTGGTGTCCCAGATGCCCCACGTGGCCACTCC
AGGGGCCTCCTGCACCCAGCATTTCCCTTCA**TGGGCT
CTTTGCTGTGAGGC**CCAGCTGGGGCCAAGGGAGGATG
GGCCAGCCACGTCCAGCCTCTGACACTAGTGTCCCTTCG
CCTTGCAG

<u>GGTGCGGCGGTGATGATGGAGAATAAGCCCATGACCCTG
AAGCTCATCATGACCTTGGCATTCACCACCCTCGGCGAA
CGTGCCTTCATGAACCGCACTGTGGGTGAGATCATGTGG
GGCTACAAGGACCCCTTGTGAATCTCATCAACAAGTACT
TTCCAGGCATGTTCCCCTTCAAGGACAAGTTCGGATTAT
TGCTGAG</u>

GTACGTGTGGCCTGGTGAGAAGCCAAAGATTCAGGCCTG
TGTCCTGTCTTCCCCTCACACAGCCTGGACACTGGTC
ACCAGCTTGCTTTGTAGCTGGCTGGGATCTAGTGGCTG
TGGGTTGTAAGTGACTGAGAACCTGACTCAAACCGGCTT
GAGTGAAA exon 5

CCTCTCGGTCCCCAGACACTGGGCATTTGGCAGTGAACC
AGATGCTGGGGGCCCTGTCCTTCTGGTGGAGGGGGAGGA
GGGCTCAGCCCAGAATGTTCAGACCAGGCCGGCTCAA
TGGCAGGCCTAAGCCTTACGATGCTGTTCCCTGCTGTGT
CTGTAG

<u>CTCAACAACTCCGACTCTGGGCTCTTCACGGTGTTCACG
GGGGTCCAGAACATCAGCAGGATCCACCTCGTGGACAAG
TGGAACGGGCTGAGCAAG</u>

GTGAGGGGCGAGAGGCGAGGGCCCTGTCGCCAGGGAGA
GGGGAGGGTGGGCCTGGCCATGGCTGCTCGGGAGTGGCA
GGGACCAGAGAGCTCCTTCTTC**CTTTGTCGTGAAGAG
GGTGC**TGGGAGGATGAACACTCTTGAAGTTGGAGGAGGG
ATTTTA

Fig. 2C exon 6

TCTCTGTGTGTCTACATAGCCTGCCCTCTTCCCACCGTG
CCAGTATTGGGAATTGAGTGGCCGTGCGTGCACCAGGGT
GAGTTAGGTGTGCAGCACCTGAGAGGGCTTATTAAGG
GGCCTTGGCCCTACTGAGGGGTCTAGTCTGGATGCTTCC
CCCCAG

<u>GTTGACTTCTGGCATTCCGATCAGTGCAACATGATCAAT</u>
<u>GGAACTTCTGGGCAAATGTGGCCGCCTTCATGACTCCT</u>
<u>GAGTCCTCGCTGGAGTTCTACAGCCCGGAGGCCTGCCG</u>

GTAATCACTGGGACTCGGGGCCTCCTGGGTTTCCTGGGT
AGCTCATGGCCAAATTCTGTGGTGTTGGCTGTGCACTT
GGAAAGCATTTTGACTCATCGTGGATTTGACTCAGTAG
CCCTTGGCACCAGCTTGAATTCTCTTTGGTCACACCACC
AAAAGC exon 7

GGAGGTCGCTGCAGCTCCGCGGGTGAGAGATGGGGGCGG
TTTGGACCCGGGAGGTGGTAGCGCCCGTGGGGAGAAGTG
GCTGGATCTGGGCAGCCTTTGGCAGGGCCTGGCTCTGGC
CGCCGGGTCTGGGTGTCCCCTCTCATCCTGTCTGTCC
CCTGCAG

<u>ATCCATGAAGCTAATGTACAAGGAGTCAGGGGTGTTTGA</u>
<u>AGGCATCCCCACCTATCGCTTCGTGGCTCCCAAAACCCT</u>
<u>GTTTGCCAACGGGTCCATCTACCCACCCAACGAAGGCTT</u>
<u>CTGCCCGTGCTGGAGTCTGGAATTCAGAACGTCAGCAC</u>
<u>CTGCAGGTTCA</u>

GTACGTGCCGTCCCTGTTCTGGGATNGCCGGAGGGTGT
TAGGTNTNGGGCACCTNAGGTTTATCTGCCCAATGCTG
TCTGCTTAATCTCTGGCTCTGTACTCTTGATAACC
CATTAAGCCAAAAATATGATGCCTCTGGGACGATATCTG

Fig. 2D exon 8

TGGGGCTTTTTACAGAATGGAGGAAGGGATCCTCTCT
GTCGGGTATTATGGTCATCGCCACGGGGGTGCCGTGCAG
ACCACAGCTCTGTGCAGACTTCCGGAGTGGCAGGACGTG
CCAATATACTGTCGTTGTATGATGTCCCCTCCCTGCCCT
TGTTGTAG

<u>GTGCCCCTTGTTTCTCTCCATCCTCACTTCCTCAACG</u>
<u>CCGACCCGGTTCTGGCAGAAGCGGTGACTGGCCTGCACC</u>
<u>CTAACCAGGAGGCACACTCCTTGTTCCTGGACATCCACC</u>
<u>CG</u>

GTGAGCCCCTGCCATCCTCTGTGGGGGGTGGGTGATTCC
TGGTTGGAGCACACCTGGCTGCCTCCTCTCTCCCCAG
GCAGAGAGCTGCTGTGGGCTGGGGTGGTGGGAAGCCTGG
CTTCTAGAATCTCGAGCCACCAAAGTTCCTTACT exon 9

CCCCAGCCTGTGGCTTGTTTTAGGTAAGATACAAGCAAG
CTCCACTGGGCAGTTAGCTGGGACGCCACCCTCTTGAC
TGGGACCAGGGAAAAGAAGGTTGACTGTGTCCCTGGA
GCTTGGGGGTGGCCAGTCTCCTCACTGTGTTTGTTGCCG
CAG

<u>GTCACGGGAATCCCCATGAACTGCTCTGTGAAACTGCAG</u>
<u>CTGAGCCTCTACATGAAATCTGTCGCAGGCATTGG</u>

GTGAGTGGGGACTGGGAACTGGGGCTGCATTGCTCATTG
AGAGATTANGTGCTCAGTGCTCCAGTGTTCCCAGAC
TCCCTGACATACCCAGGAAACAGGGCATGGGGAAGGG
AGAGGGTCCTATTGGGGGTGGAATCCAGTCCCTGCTGAT
CTTCTC

Fig. 2E exon 10

ATGGCTCCTAAAGTGTTTCAGCTCATTGTTTATATTT**GG
TGGTGAGGGTTTAGTGTG**TGCAAAATTATACTAAACC
TGTTTAGATGTTGTATTCAAGCAGAATTAGATCAAGTTT
GGGTGTAAGACTTTGTTCCAACACCTATGTCTTGCTTAT
TTCCAG

<u>ACAAACTGGGAAGATTGAGCCTGTGGTCCTGCCGCTGCT
CTGGTTTGCAGAG</u>

GTAAGGGTGCGTTGGGCACAGCGTCGGGGGCTTTTGTTA
ATAGCCAATGTGGGCATTT**GAGGCAGGAGGCGGGGGG
AG**CACCTTGTAGAAGGGAGAGGGCTGAGCCAGGGTAAC
CGGACTGTTACATGGACCAGCGTATCATACACTTCACCC
TGTC exon 11

CCTGGAGGGAGGAGGTCCCTGGCAGGCTCCAACACATGC
TTTAGCCGGGAAGCTTGAGGTGGGGAAAAGCTGAGGCGG
GCACAGAGGAAGGTGTTGGGTGGCATCTGCGCTGTAG
CCCGCAGCGTGCGGCCCAGCTCATGTGTTTGTCATTCT
GTCTCCTCAG

<u>AGCGGGGCCATGGAGGGGGAGACTCTTCACACATTCTAC
ACTCAGCTGGTGTTGATGCCCAAGGTGATGCACTATGCC
CAGTACGTCCTCCTGGCGCTGGGCTGCGTCCTGCTGCTG
GTCCCTGTCATCTGCCAAATCCGGAGCCAA</u>

GTAGGTGCTGGCCAGAGGGCAGCCCGGGCTGACAGCCAT
TCGCTTGCCTGCTGGGGGAAAGGGGCCTCAGATCGGACC
CTCTGGCCAACCGCAGCCTGGAGCCCACCTCCAGCAG
CAGTCCTGCGTCTCTGCCGGAGTGGGAGCGGTCACTGCT
GGGGG

Fig. 2F exon 12

CCCCACATCTCAGCCACCTGCAATCGTTGAGGGTTGTTG
GACTCTAAACTTATGTGCCTTTCCTGTTTCCTCTTTGCC
TTTTGCAAATTGAAGAACCGTGTAAAACCATTTTTAT
GTGGCTTCAACGTCAACTATAAATTAGCTTGGTTATCTT
CTAG

<u>GAGAAATGCTATTTATTTTGGAGTAGTAGTAAAAGGGC</u>
<u>TCAAAGGATAAGGAGGCCATTCAGGCCTATTCTGAATCC</u>
<u>CTGATGACATCAGCTCCAAGGGCTCTGTGCTGCAGGAA</u>
<u>GCAAAACTGTAG</u>

GTGGGTACCAGGTAATGCCGTGCGCCTCCCCGCCCCCTC
CCATATCAAGTAGAATGCTGGCGGCTTAAAACATTTGGG
GTCCTGCTCATTCCTTCAGCCTCAACTTCACCTGGAG
TGTCTACAGACTGAAGATGCATATTTGTGTATTTTGCTT
TTGGAGAAA

```
  F   L   D   I   H   P   ...V...  G   I   P   M   N   C   S   V   K   L   Q   L        390
  TTC CTG GAC ATC CAC CCG GTC ACG GGA ATC CCC ATG AAC TGC TCT GTG AAA CTG CAG CTG       1288
                            └─exon 9
  S   L   Y   M   K   S   V   A   G   I   ...G... Q   T   G   E   I   E   P   V   V    410
  AGC CTC TAC ATG AAA TCT GTC GCA GGC ATT GGA CAA ACT GGG AAG ATT GAG CCT GTG GTC       1348
                                        └─exon 10
  L   P   L   W   P   A   ...E... S   G   A   M   E   G   Y   L   M   T   F            430
  CTG CCG CTC TGG CCT TTT GCA GAG AGC GGG GCC ATG GAG GGG TAT CTT ATG ACA TTC           1408
                        └─exon 11
  Y   T   Q   L   V   M   P   K   V   M   H   Y   A   Q   R   S   E   V   L   A        450
  TAC ACT CAG CTG GTG ATG CCC AAG GTG ATG CAC TAT GCC CAG CGG GAG GTC CTC GCG           1468
  L   G   C   V   L   L   L   P   V   I   ...Q... E   K   C                             470
  CTG GGC TGC GTC CTG CTG CTG CCT GTC ATC CAA GAG AAA TGC                               1528
                                        └─exon 12
  Y   L   F   W   S   S   S   K   G   S   K   A   I   Q   A   Y                        490
  TAT TTA TTT TGG AGT AGT AGT AAG GGC TCA AAG GAT AAG GAG GCC ATT CAG GCC TAT           1588
                                                                            ↑ exon 12
  S   E   S   L   M   T   S   A   P   K   G   S   V   L   Q   E   A   K   L   *        510
  TCT GAA TCC CTG ATG ACA TCA GCT CCC AAG GGC TCT GTG CTG CAG GAA GCA AAA CTG TAG      1648
  GCTCCTGAGGACACCGTGAGCCAGGCCTGACCGCTGGGCCTGCCGCTGACCCCCAGCCCCCTACACCCGCTTCTCC         1727
  CGGACTCTCCCAGCAGACAGCCCCCAGCCCCCAGCCTCTGAGCCCTTCCCAGCTGCCATGTCCCTGTTGCACACCTGCACA    1806
  CACGCCCTGGCACACATACACACATGCGTGCAGGCTTGTGCAGACACTCAGGGATGGAGCTGCTGAAGGGACTTGT         1885
```

Fig. 3B-1

```
AGGGAGAGGCTCGTCAACAACCACTGTTCTGGAACCTTCTCTCCACGTGGCCCTGACCACAGGGGCTGTGGG   1964
TCCTGCGCGTCCCCTTCCTCGGGTGAGCCTGGCCTGTCCCGTTCAGCCGTTGGGCCCAGGCTTCCTCCCTCCAACGTGAA   2043
ACACTGCAGTCCCGGTGTGGTGGCTCCCCATGCAGGACGGGCCAGGCTGGGAGTGCCGCCTTCCTGTGCCAAATTCAGT   2122
GGGGACTCAGTGCCCAGGCCCCAGGCCCACGAGCTTTGGCCTTGGTGTCTACCTGCCAGGCAAAGCGCCTTTACACAG   2201
GCCTCGGAAAACAATGGAGTGAGCACAAGATGCCCTGTGCAGCTGCCCGAGGGTCTCCGCCCACCCGGCCGGACTTTG   2280
ATCCCCCCGAAGTCTTCACAGGCACTYTYTCCTCCAGCCTAAACTGACATCATCCTAT   2359
GGACTGAGCCGGCCACTYTYTGGCCGAAGTGGCCGCAGGCTGTGCCCACCCCCGAGCTGCCCCTGCCTTCCACCCCT   2438
CAGATTATAGGTGCCCAGGCTGAGGTGAAGAGAGGCCCTGGGGGCCCTGAGTTTATCATCTTTGAAAATAATTCACTCTTGAGACCCTGGGGCAAACC   2517
TGTGACCCTTTTCTACTGAATAGAAATGAGTTTTATCATCTTTGAAGTAATAAACGTTTA   2596
AAAAAATGGGAAAAAAAAAAAAAAAAAAAAA   2630
```

Fig. 3B-2

DIAGNOSTIC ASSAYS AND KITS FOR BODY MASS DISORDERS ASSOCIATED WITH A POLYMORPHISM IN AN INTRON SEQUENCE OF THE SR-BI GENE

1. BACKGROUND OF THE INVENTION

Obesity is defined as the excessive accumulation of body fat. A body weight 20% over that in standard height-weight tables is arbitrarily considered obesity (except for certain heavily muscled persons).

The prevalence of obesity in the U.S.A. is 24% of men and 27% of women. There are great differences in age, socioeconomic status, and race. For example, there is a two fold increase in the prevalence of obesity between the ages of 20 and 55. Obesity is also far more common among black than white women, reaching a value of 60% among middle-aged black women ("The Merck Manual of Diagnosis and Therapy", Berkow et al., $16^{th}$ Edition, 1992, Merck Research Laboratories).

Obesity and overweight are largely genetically determined and are strongly conditioned by available palatable food and sendentariness. A child of two obese parents has about 80% chance of becoming obese, whereas that risk is only 15% for a child of two normal weight parents. Twin and adoption studies have also shown that genetic factors are critical determinants of obesity.

Endocrine and metabolic factors can also be associated with developing and maintaining obesity, e.g., adipose tissue proliferation in hyperadrenocorticism is due to corticosteroid excess and leads to increased gluconeogenesis and a correspondingly greater demand for insulin, which, in turn, stimulates lipogenesis.

Obesity has numerous medical consequences. These vary depending on the severity of obesity. Severely obese individuals (weighing 60% over a normal weight) have a high risk of developing cardiorespiratory problems. They are also at risk of developing chronic hypoventilation, which can lead to hypercapnia, pulmonary hypertension, and heart failure. Severe episodic hypoxia can cause arrhythmias and sudden death is 10 times more common in the severely obese. Severely obese individuals are also at increase risk of suffering from obstructive sleep apnea, pickwickian syndrome (i.e., daytime hypoventilation, somnolence, polycythemia, and cor pulmonale), and renal vein thrombosis. In addition, a severely obese individual suffers psychological consequences of the disorder ("Cecil Essentials of Medicine", Andreoli et al., Third Edition, 1993, W.B. Saunders Company).

Moderate obesity (corresponding to a weight between 20–60% above normal weight) poses increased risk of early mortality. Obese individuals suffer more frequently than non obese individuals from hypertension. Type II diabetes mellitus can also be aggravated by excess weight. Obesity also increases the risk of cholelithiasis and endometrial carcinoma.

Obesity is often associated with high triglyceride and low high density lipoprotein (HDL) concentrations and thus renders an obese subject susceptible to cardiavascular diseases, such as ischemia, restenosis, congestive heart failure, and atherosclerosis.

The availability of a test allowing to predict whether a person is at risk of becoming obese would greatly enhance prevention and treatment of obesity and thus of the multiple medical consequences resulting from obesity.

2. SUMMARY OF THE INVENTION

Figure 3A-1:
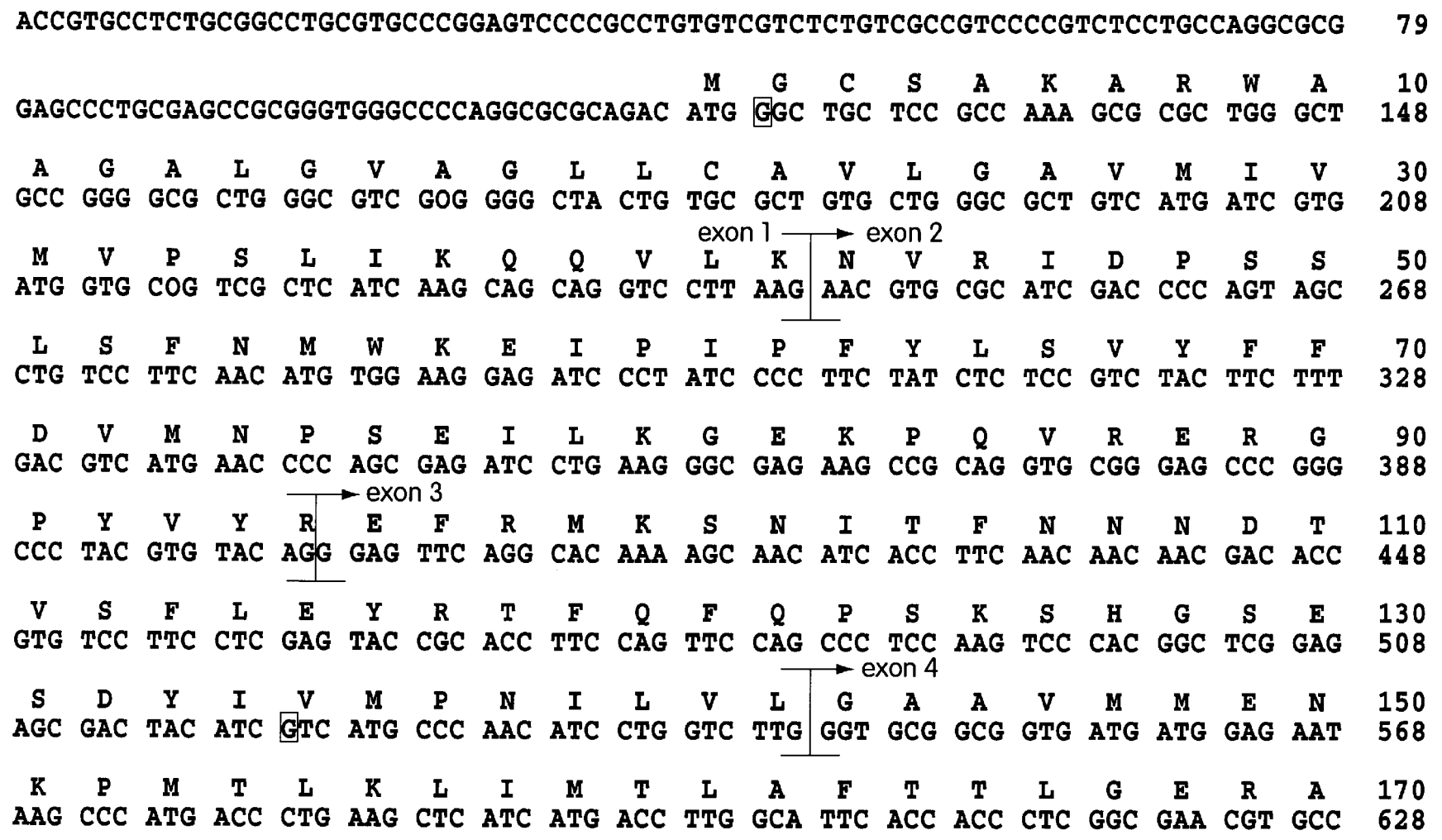
Figure 3A-2:
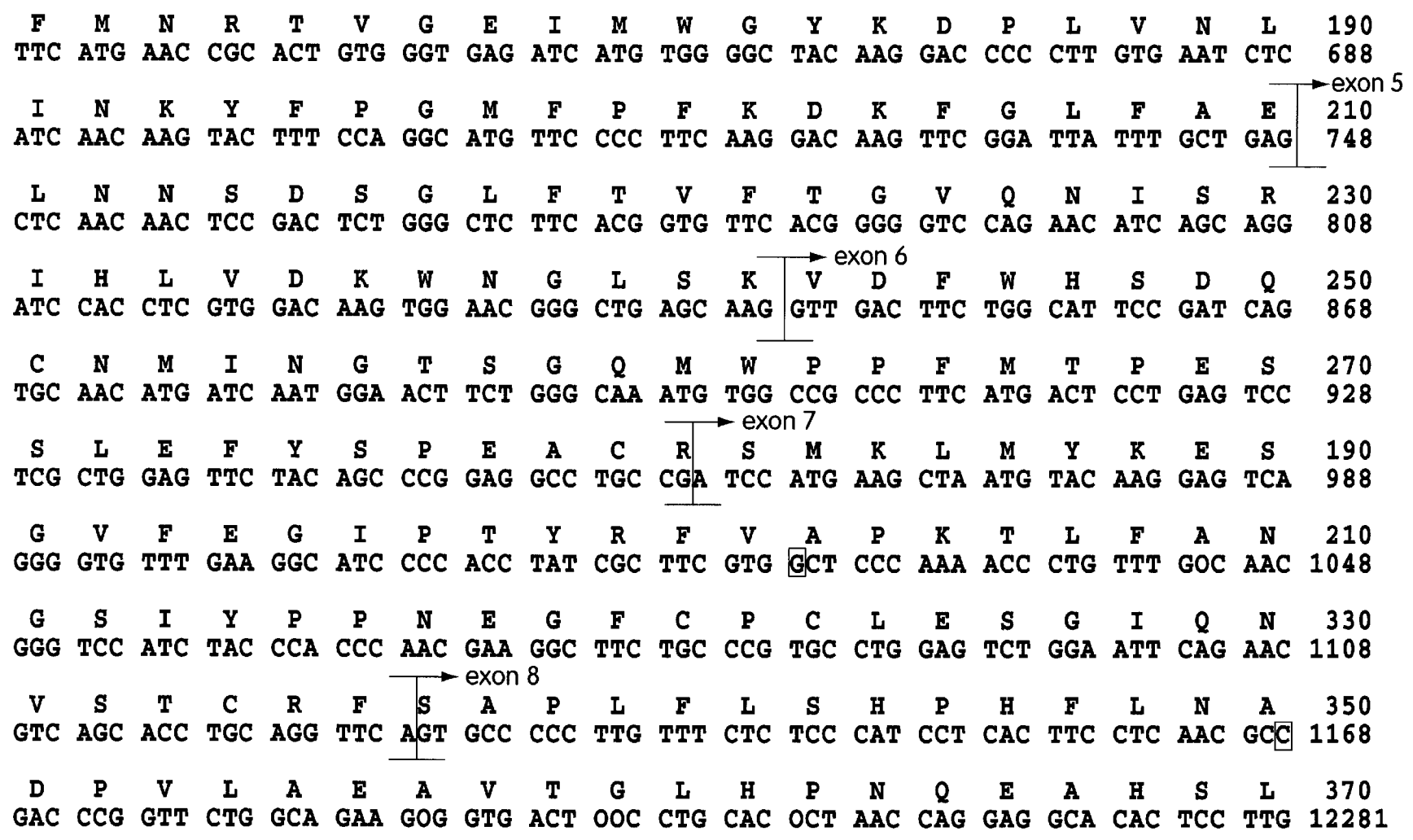

The present invention is based at least in part on the discovery that a specific allele of a polymorphic region of the human SR-BI gene is associated with an abnormally high body mass, e.g., obesity. The SR-BI receptor (Scavenger Receptor-BI) is a scavenger receptor that mediates endocytosis of unmodified and modified lipoproteins, e.g., LDL, acetylated LDL, oxidized LDL (Acton et al. (1994) J. Biol. Chem. 269:21003), HDL (Acton, S. et al., (1996) *Science* 271:518–520), anionic phospholipids (Rigotti et al. (1995) J. Biol. Chem. 270:16221), negatively charged liposomes and apoptotic cells (Fukasawa et al. (1996) Exp. Cell Res. 222:246). The human SR-BI gene contains 12 coding exons and one non coding exon (exon 13). The structure of the gene and the position of the introns relative to the nucleotide sequence of the exons are shown in FIGS. 1, 2, and 3.

To identify diseases or disorders which are associated with specific polymorphic regions of the SR-BI gene, a genetic study of a specific population of individuals (142 Spanish individuals) which were chosen because they have a known HDL level (either low, normal, or high), age, body mass index, and triglyceride levels was performed. This study revealed that a specific allelic variant of a polymorphic region of the SR-BI gene is associated with a high body mass, in particular in premenopausal women. The polymorphism is a nucleotide polymorphism consisting of a substitution of the cytidine at position 54 of intron 5 with a thymidine. The polymorphism was found in about 24% of the population.

Accordingly, in a preferred embodiment, the invention provides a method for determining whether a subject has, or is at risk of developing, a body mass disorder, e.g. an abnormally high body mass, comprising determining the identity of the allelic variant of a polymorphic region of the SR-BI gene of the subject. The method further comprises comparing the nucleotide sequence of the allelic variant of the subject with the nucleotide sequence of allelic variants associated with body mass disorders, to thereby determine whether the subject has an allelic variant of a polymorphic region of an SR-BI gene associated with a body mass disorder. In a preferred embodiment, the polymorphic region is located in an intron, such as intron 5. In an even more preferred embodiment, the polymorphic region is a nucleotide polymorphism, which is preferably located at position 54 of intron 5. Even more preferably, according to the method of the invention, a subject has or is at risk of developing a high body mass, e.g., obesity, if the subject has a nucleotide other than a cytidine at position 54 on intron 5 in the SR-BI gene, e.g., a thymidine.

The method of the invention can comprise determining the identity of the allelic variant of a polymorphic region by contacting a nucleic acid of the subject with at least one probe or primer which is capable of hybridizing to an allelic variant of the polymorphic region, e.g., an allelic variant which comprises a thymidine at position 54 of intron 5 of the SR-BI gene. In other preferred embodiments, of the invention the probe or primer is capable of hybridizing to a region which is adjacent to the polymorphic region, of which specific alleles are associated with a body mass disorder, such that hybridization is informative of the identity of the allelic variant of the polymorphic region. In a preferred embodiment, the probe or primer has a nucleotide sequence from about 15 to about 30 nucleotides. In another preferred embodiment, the probe or primer is a single stranded nucleic acid, which can further be labeled.

According to the method of the invention, the identity of the allelic variant of a polymorphic region can be determined by single-stranded conformation polymorphism. The identity of an allelic variant can also be determined by allele specific hybridization, primer specific extension, oligonucleotide ligation assay, or restriction enzyme site analysis.

The invention further provides a kit for determining whether a subject has, or is at risk of developing, a body mass disorder. In a preferred embodiment, the kit comprises a probe or primer which is capable of hybridizing to an SR-BI gene and thereby identifying whether the SR-BI gene contains an allelic variant of a polymorphic region which is associated with the body mass disorder. The kit preferably contains instructions for use in diagnosing a subject as having, or having a predisposition, towards developing a body mass disorder. In a preferred embodiment, the body mass disorder is an abnormally high body mass. In a preferred embodiment, the polymorphic region is a nucleotide polymorphism. In an even more preferred embodiment, the nucleotide polymorphism is located in an intron, such as intron 5. In a even more preferred embodiment of the invention, the polynucleotide polymorphism is located at nucleotide 54 of intron and is preferably a substitution of a cytidine with a thymidine.

In one embodiment, the kit comprises a probe or primer which is capable of hybridizing to the polymorphic region of the SR-BI gene. The probe or primer is preferably capable of hybridizing to a region of the human SR-BI comprising nucleotide 54 of intron 5, such as a region of the human SR-BI gene, wherein nucleotide 54 of intron 5 is a thymidine. In another embodiment, the kit comprises a primer which is capable of hybridizing to a region of an SR-BI gene which is adjacent to the polymorphic region.

Also within the scope of the invention are kits comprising a second probe or primer, kits wherein the probe or primer is from about 15 to about 30 nucleotides, kits wherein the probe or primer is a single stranded nucleic acid, and kits wherein the probe or primer is labeled.

Other features and advantages of the invention will be apparent from the following detailed description and claims.

3. BRIEF DESCRIPTION OF THE FIGURES

FIG. 1 is a schematic depiction of the chromosomal structure of the human SR-BI gene indicating the introns (I through 12) and exons (I–XIII). Black boxes represent coding exons (exons I–XII) and the white box represents the non-coding exon (exon XIII).

FIGS. 2(A–G) shows the nucleotide sequence of the exons (underlined sequence) of the human SR-BI gene, portions of the introns which are adjacent to the exons, and 3' promoter sequence (SEQ ID Nos. 5–40). The putative 5' end of the cDNA, as predicted by GRAIL is indicated in italics. The TATA-like box is indicated in italics and is boxed. Bold sequences correspond to the nucleotide sequence or the complement of the nucleotide sequence of preferred primers for amplifying each of the exons or a promoter region. The nucleotide polymorphism in intron 5 is boxed.

FIGS. 3(A–B) shows the nucleotide sequence of the full length human SR-BI cDNA (SEQ ID NO. 1) and the position of introns 1–12 relative to the nucleotide sequence of the exons.

4. DETAILED DESCRIPTION OF THE INVENTION 4.1. General

The present invention is based at least in part on the discovery that a specific allele of a polymorphic region of the human SR-BI gene is associated with a high body mass index.

As shown in FIG. 1, the human SR-BI gene is at least 50 kilobase pairs long and has 12 coding exons, one non-coding exon (exon 13), and 12 introns. The exons are numbered 1 to 13 from 5' to 3' and the introns are labeled 1 through 12 from 5' to 3'. Exon 1 corresponds to the first exon located downstream of the promoter and contains the initiation codon. Intron 1 is located immediately downstream of exon I (see FIG. 1). The position of the introns relative to the nucleotide sequence of the full length cDNA encoding, SR-BI is shown in FIG. 2. The nucleotide sequence of the human SR-BI cDNA, shown in FIG. 3 and in SEQ ID NO. 1 encodes a protein of 509 amino acids. SEQ ID NO. 1 contains the nucleotide sequence of the cDNA disclosed in Calvo and Vega (1993) J. Biol. Chem. 268:18929, and contains in addition a complete 5' end. The amino acid sequence of the protein set forth in SEQ ID NO. 2 is identical to the Cla-I protein disclosed in Calvo and Vega (1993) J. Biol. Chem. 268:18929. As set forth in Calvo and Vega, supra, differential splicing of the human SR-BI gene also results in a short mRNA lacking 300 nucleotides located 126 nucleotides downstream of the initiation codon, i.e., lacking exons 2 and 3 set fort in FIG. 3, which encodes a protein of 409 amino acids. The shorter protein is referred to herein as "splice variant". The nucleotide sequence of a full length cDNA encoding the splice variant is set forth in SEQ ID NO. 3 and the amino acid sequence of the SR-BI splice variant protein encoded by this nucleotide sequence is set forth in SEQ ID NO. 4. The splice variant is rare relative to the 509 amino acid SR-BI protein.

FIG. 2 shows the nucleotide sequence of the 3' end of the SR-BI promoter. Additional promoter sequence is disclosed in U.S. patent application Ser. No. 08/812,204 by Acton, incorporated herein by reference.

Set forth below in Table I are the locations and sizes of the exons in the human SR-BI gene relative to the nucleotide sequence of a full length cDNA encoding human SR-BI protein (SEQ ID NO. 1), in which nucleotide 1 corresponds to the first nucleotide in the isolated transcript. Table I also indicates the portions of the human SR-BI protein encoded by each of these exons. Amino acid 1 is the initiating methionine. Also indicated is the length of the intron located downstream of each of the exons.

TABLE I

| | Nucleotide position | Amino acid position | Size of intron |
|---|---|---|---|
| Exon 1 | 1–244 | 1–42 | intron 1: >2827 |
| Exon 2 | 245–402 | 43–95 | intron 2: 2429 |
| Exon 3 | 403–544 | 95–142 | intron 3: 567 |
| Bxon 4 | 545–748 | 143–210 | intron 4: 2229 |
| Exon 5 | 749–844 | 211–242 | intron 5: 1580 |
| Exon 6 | 845–960 | 243–281 | intron 6: >10532 |
| Exon 7 | 961–1127 | 281–337 | intron 7: >3985 |
| Exon 8 | 1228–1246 | 337–376 | intron 8: >11321 |
| Exon 9 | 1247–1320 | 377–401 | intron 9: 7562 |
| Exon 10 | 1321–1372 | 401–418 | intron 10: 902 |
| Exon 11 | 1373–1519 | 419–467 | intron 11: 3547 |
| Exon 12 | 1520–1648 | 468–509 | intron 12: >4578 |
| Exon 13 | 1649–2630 | | |

FIG. 2 shows the nucleotide sequence of portions of the introns which are adjacent to the exons. The nucleotide sequence of each of the exons and adjacent portions of introns shown in FIG. 2 are set forth in SEQ ID Nos. 5 to 16. The portions of each of the introns shown in FIG. 2 are set forth in SEQ ID Nos. 18 to 40. For convenience, the identity of the sequences referred to as SEQ ID Nos. 1 to 40 are set forth below in Table II:

TABLE II

| | |
|---|---|
| SEQ ID NO. 1 | full length cDNA encoding human SR-BI; |
| SEQ ID NO. 2 | full length amino acid sequence of human SR-BI protein; |
| SEQ ID NO. 3 | full length cDNA encoding splice variant of human SR-BI (Calvo and Vega, supra); |
| SEQ ID NO. 4 | full length amino acid sequence of splice variant of human SR-BI protein (Calvo and Vega, supra); |
| SEQ ID NO. 5 | 3' end of promoter, exon 1, and 5' end of intron 1; |
| SEQ ID NO. 6 | 3' end of intron 1, exon 2, and 5' end of intron 2; |
| SEQ ID NO. 7 | 3' end of intron 2, exon 3, and 5' end of intron 3; |
| SEQ ID NO. 8 | 3' end of intron 3, exon 4, and 5' end of intron 4; |
| SEQ ID NO. 9 | 3' end of intron 4, exon 5, and 5' end of intron 5; |
| SEQ ID NO. 10 | 3' end of intron 5, exon 6, and 5' end of intron 6; |
| SEQ ID NO. 11 | 3' end of intron 6, exon 7, and 5' end of intron 7; |
| SEQ ID NO. 12 | 3' end of intron 7, exon 8, and 5' end of intron 8; |
| SEQ ID NO. 13 | 3' end of intron 8, exon 9, and 5' end of intron 9; |
| SEQ ID NO. 14 | 3' end of intron 9, exon 10, and 5' end of intron 10; |
| SEQ ID NO. 15 | 3' end of intron 10, exon 11, and 5' end of intron 11; |
| SEQ ID NO. 16 | 3' end of intron 11, exon 12, and 5' end of intron 12; |
| SEQ ID NO. 17 | 3' end of promoter; |
| SEQ ID NO. 18 | 5' end of intron 1; |
| SEQ ID NO. 19 | 3' end of intron 1; |
| SEQ ID NO. 20 | 5' end of intron 2; |
| SEQ ID NO. 21 | 3' end of intron 2; |
| SEQ ID NO. 22 | 5' end of intron 3; |
| SEQ ID NO. 23 | 3' end of intron 3; |
| SEQ ID NO. 24 | 5' end of intron 4; |
| SEQ ID NO. 25 | 3' end of intron 4; |
| SEQ ID NO. 26 | 5' end of intron 5; |
| SEQ ID NO. 27 | 3' end of intron 5; |
| SEQ ID NO. 28 | 5' end of intron 6; |
| SEQ ID NO. 29 | 3' end of intron 6; |
| SEQ ID NO. 30 | 5' end of intron 7; |
| SEQ ID NO. 31 | 3' end of intron 7; |
| SEQ ID NO. 32 | 5' end of intron 8; |
| SEQ ID NO. 33 | 3' end of intron 8; |
| SEQ ID NO. 34 | 5' end of intron 9; |
| SEQ ID NO. 35 | 3' end of intron 9; |
| SEQ ID NO. 36 | 5' end of intron 10; |
| SEQ ID NO. 37 | 3' end of intron 10; |
| SEQ ID NO. 38 | 5' end of intron 11; |
| SEQ ID NO. 39 | 3' end of intron 11; and |
| SEQ ID NO. 40 | 5' end of intron 12. |

An analysis of the human SR-BI gene in a population of individuals chosen because these individuals had a known age, known HDL levels, known body mass index, and known triglycerides level revealed the association between a specific SR-BI allele of a polymorphic region and a body mass. The polymorphic region in the human SR-BI gene is located in the fifth intron. More specifically, the polymorphism corresponds to the replacement of the cytidine at position 54 of the intron (position 1 being defined as the first nucleotide in the intron) with a thymidine. This nucleotide substitution destroys the ApaI restriction site which is present when the nucleotide at position 54 is a cytidine. The nucleotide sequence of the 5' end of intron 5 of this allele is set forth in SEQ ID NO. 65 (SEQ ID NO. 65 is identical to SEQ ID NO. 26, except for nucleotide 54 which is a thymidine). As set forth in the Examples, this SR-BI allele is associated with a high body mass index.

Accordingly, the invention provides methods for determining the identity of the allelic variant of a polymorphic region, said polymorphic region having allelic variants which are associated with body mass disorders. Such methods can be used, for example, to determine whether a subject has or is at risk of developing a disease or condition associated with one or more specific alleles of polymorphic regions of an SR-BI gene, e.g., abnormal body mass. In a preferred embodiment, the disease or condition is caused or contributed to by an aberrant SR-BI bioactivity. Other aspects of the invention are described below or will be apparent to one of skill in the art in light of the present disclosure.

4.2 Definitions

For convenience, the meaning of certain terms and phrases employed in the specification, examples, and appended claims are provided below.

The term "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation.

The term "allelic variant of a polymorphic region of an SR-BI gene" refers to a region of an SR-BI gene having one of several nucleotide sequences found in that region of the gene in other individuals.

"Biological activity" or "bioactivity" or "activity" or "biological function", which are used interchangeably, for the purposes herein when applied to SR-BI means an effector or antigenic function that is directly or indirectly performed by an SR-BI polypeptide (whether in its native or denatured conformation), or by any subsequence (fragment) thereof. Biological activities include binding to a ligand, e.g., a lipid or lipoprotein, such as LDL or modified forms thereof, or HDL or modified forms thereof. Other molecules which can bind an SR-BI receptor include anionic molecules, such as anionic phospholipids, negatively charged liposomes, and apoptotic cells. Another biological activity of an SR-BI protein includes endocytosis of a ligand interacting with the receptor. A biological activity is also intended to include binding to a protein, such as binding to the cytoplasmic domain of SR-BI. Yet other biological activities include signal transduction from the receptor, modulation of expression of genes responsive to binding of a ligand to an SR-BI receptor, and other biological activities, whether presently known or inherent. An SR-BI bioactivity can be modulated by directly affecting an SR-BI protein. Alternatively, an SR-BI bioactivity can be modulated by modulating the level of an SR-BI protein, such as by modulating expression of an SR-BI gene. Antigenic functions include possession of an epitope or antigenic site that is capable of cross-reacting with antibodies raised against a naturally occurring or denatured SR-BI polypeptide or fragment thereof.

Biologically active SR-BI polypeptides include polypeptides having both an effector and antigenic function, or only one of such functions. SR-BI polypeptides include antagonist polypeptides and native SR-BI polypeptides, provided that such antagonists include an epitope of a native SR-BI polypeptide. An effector function of SR-BI polypeptide can be the ability to bind to a ligand, e.g., a lipid or modified form thereof.

As used herein the term "bioactive fragment of a SR-BI protein" refers to a fragment of a full-length SR-BI protein, wherein the fragment specifically mimics or antagonizes the activity of a wild-type SR-BI protein. The bioactive fragment preferably is a fragment capable of binding to a second molecule, such as a ligand.

The term "an aberrant activity" or "abnormal activity", as applied to an activity of a protein such as SR-BI, refers to an activity which differs from the activity of the wild-type or native protein or which differs from the activity of the protein in a healthy subject. An activity of a protein can be aberrant because it is stronger than the activity of its native counterpart. Alternatively, an activity can be aberrant because it is weaker or absent related to the activity of its native counterpart. An aberrant activity can also be a change in an activity. For example an aberrant protein can interact with a different protein relative to its native counterpart. A cell can have an aberrant SR-BI activity due to overexpression or underexpression of the gene encoding SR-BI. An aberrant SR-BI activity can result, e.g., from a mutation in the protein, which results, e.g., in lower or higher binding affinity of a lipid to the mutated SR-BI. An aberrant SR-BI activity can also result from a lower or higher level of SR-BI receptor on cells, which can result, e.g., from a mutation in the SR-BI 5' flanking region of the SR-BI gene or any other regulatory element of the SR-BI gene, such as a regulatory element located in an intron. Accordingly, an aberrant SR-BI activity can result from an abnormal SR-BI promoter activity.

The terms "abnormal SR-BI promoter activity", "aberrant SR-BI promoter activity", "abnormal SR-BI transcriptional activity" and "aberrant SR-BI transcriptional activity", which are used interchangeably herein, refer to the transcriptional activity of an SR-BI promoter which differs from the transcriptional activity of the same promoter in a healthy subject. An abnormal SR-BI activity can result from a higher or lower transcriptional activity than that in a healthy subject. An aberrant SR-BI promoter activity can result, e.g., from the presence of a genetic lesion in a regulatory element, such as in a regulatory element located in the promoter. An "aberrant SR-BI promoter activity" is also intended to refer to the transcriptional activity of an SR-BI promoter which is functional (capable of inducing transcription of a gene to which it is operably linked) in tissues or cells in which the "natural" or wild-type SR-BI promoter is not functional or which is non functional in tissues or cells in which the "natural" or wild-type SR-BI promoter is functional. Thus, a tissue distribution of SR-BI in a subject which differs from the tissue distribution of SR-BI in a "normal" or "healthy" subject, can be the result of an abnormal transcriptional activity from the SR-BI promoter region. Such an abnormal transcriptional activity can result, e.g., from one or more mutations in a promoter region, such as in a regulatory element thereof. An abnormal transcriptional activity can also result from a mutation in a transcription factor involved in the control of SR-BI gene expression.

The term "body mass index" or "BMI" refers to the ratio of weight (kg)/height (m$^2$) and can be used to define whether a subject is overweight. Typically, a subject is underweight if he has a BMI<20; normal if he has a BMI of 20–25, overweight if he has a BMI of 25–30, obese if he has a BMI of 30–40 and severely obese if he has a BMI>40.

As used herein, a subject has an "abnormal body mass" or "abnormal body mass index" or "aberrant body mass" or "aberrant body mass index" if his body mass index is outside the range defined for a healthy or normal subject, i.e., BMI of 20–25. A disorder of body mass include any disorder affecting the body mass of a subject such that his body mass is outside the normal range. For example, obesity is a disorder of body mass. Wasting or cachexia is also a disorder of body mass. An abnormal body mass index can have a hormonal origin, e.g., in premenopausal women.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

The term "a homolog of a nucleic acid" refers to a nucleic acid having a nucleotide sequence having a certain degree of homology with the nucleotide sequence of the nucleic acid or complement thereof. A homolog of a double stranded nucleic acid having SEQ ID NO. x is intended to include nucleic acids having a nucleotide sequence which has a certain degree of homology with SEQ ID NO. x or with the complement thereof. Preferred homologs of nucleic acids are capable of hybridizing to the nucleic acid or complement thereof.

The term "interact" as used herein is meant to include detectable interactions between molecules, such as can be detected using, for example, a hybridization assay. The term interact is also meant to include "binding" interactions between molecules. Interactions may be, for example, protein-protein, protein-nucleic acid, protein-small molecule or small molecule-nucleic acid in nature.

The term "intronic sequence" or "intronic nucleotide sequence" refers to the nucleotide sequence of an intron or portion thereof.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "lipid" shall refer to a fat or fat-like substance that is insoluble in polar solvents such as water. The term "lipid" is intended to include true fats (e.g. esters of fatty acids and glycerol); lipids (phospholipids, cerebrosides, waxes); sterols (cholesterol, ergosterol) and lipoproteins (e.g. HDL, LDL and VLDL).

The term "locus" refers to a specific position in a chromosome. For example, a locus of an SR-BI gene refers to the chromosomal position of the SR-BI gene.

The term "modulation" as used herein refers to both upregulation, (i.e., activation or stimulation), for example by agonizing, and downregulation (i.e. inhibition or suppression), for example by antagonizing of a bioactivity (e.g. expression of a gene).

The term "molecular structure" of a gene or a portion thereof refers to the structure as defined by the nucleotide content (including deletions, substitutions, additions of one or more nucleotides), the nucleotide sequence, the state of methylation, and/or any other modification of the gene or portion thereof.

The term "mutated gene" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between that of a homozygous and that of a heterozygous (for that gene) subject, the mutation is said to be co-dominant.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine", "cytidine", "guanosine", and "thymidine" are used. It is understood that if the nucleic acid is RNA, a nucleotide having a uracil base is uridine.

The term "nucleotide sequence complementary to the nucleotide sequence set forth in SEQ ID NO. x" refers to the nucleotide sequence of the complementary strand of a nucleic acid strand having SEQ ID NO. x. The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID NO. x refers to the complementary strand of the strand having SEQ ID NO. x or to any nucleic acid having the nucleotide sequence of the complementary strand of SEQ ID NO. x. When referring to a single stranded nucleic acid having the nucleotide sequence SEQ ID NO. x, the complement of this nucleic acid is a nucleic acid having a nucleotide sequence which is complementary to that of SEQ ID NO. x. The nucleotide sequences and complementary sequences thereof are always given in the 5' to 3' direction. The term "complement" and "reverse complement" are used interchangeably herein.

A "non-human animal" of the invention can include mammals such as rodents, non-human primates, sheep, goats, horses, dogs, cows, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which an exogenous sequence is found, or in which an exogenous sequence is expressed in some but not all cells of the animal. The term "tissue-specific chimeric animal" indicates that an exogenous sequence is present and/or expressed or disrupted in some tissues, but not others.

The term "operably linked" is intended to mean that the promoter is associated with the nucleic acid in such a manner as to facilitate transcription of the nucleic acid from the promoter.

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long.

A "polymorphic gene" refers to a gene having at least one polymorphic region.

The terms "protein", "polypeptide" and "peptide" are used interchangeably herein when referring to a gene product.

The term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

A "regulatory element", also termed herein "regulatory sequence is intended to include elements which are capable of modulating transcription from a basic promoter and include elements such as enhancers and silencers. The term "enhancer", also referred to herein as "enhancer element", is intended to include regulatory elements capable of increasing, stimulating, or enhancing transcription from a basic promoter. The term "silencer", also referred to herein as "silencer element" is intended to include regulatory elements capable of decreasing, inhibiting, or repressing transcription from a basic promoter. Regulatory elements are typically present in 5' flanking regions of genes. However, regulatory elements have also been shown to be present in other regions of a gene, in particular in introns. Thus, it is possible that SR-BI genes have regulatory elements located in introns, exons, coding regions, and 3' flanking sequences. Such regulatory elements are also intended to be encompassed by the present invention and can be identified by any of the assays that can be used to identify regulatory elements in 5' flanking regions of genes.

The term "regulatory element" further encompasses "tissue specific" regulatory elements, i.e., regulatory elements which effect expression of the selected DNA sequence preferentially in specific cells (e.g., cells of a specific tissue). Gene expression occurs preferentially in a specific cell if expression in this cell type is significantly higher than expression in other cell types. The term "regulatory element" also encompasses non-tissue specific regulatory elements, i.e., regulatory elements which are active in most cell types. Furthermore, a regulatory element can be a constitutive regulatory element, i.e., a regulatory element which constitutively regulates transcription, as opposed to a regulatory element which is inducible, i.e., a regulatory element which is active primarily in response to a stimulus. A stimulus can be, e.g., a molecule, such as a hormone, cytokine, heavy metal, phorbol ester, cyclic AMP (cAMP), or retinoic acid.

Regulatory elements are typically bound by proteins, e.g., transcription factors. The term "transcription factor" is intended to include proteins or modified forms thereof, which interact preferentially with specific nucleic acid sequences, i.e., regulatory elements, and which in appropriate conditions stimulate or repress transcription. Some transcription factors are active when they are in the form of a monomer. Alternatively, other transcription factors are active in the form of a dimer consisting of two identical proteins or different proteins (heterodimer). Modified forms of transcription factors are intended to refer to transcription factors having a post-translational modification, such as the attachment of a phosphate group. The activity of a transcription factor is frequently modulated by a post-translational modification. For example, certain transcription factors are active only if they are phosphorylated on specific residues. Alternatively, transcription factors can be active in the absence of phosphorylated residues and become inactivated by phosphorylation. A list of known transcription factors and their DNA binding site can be found, e.g., in public databases, e.g., TFMATRIX Transcription Factor Binding Site Profile database.

As used herein, the term "specifically hybridizes" or "specifically detects" refers to the ability of a nucleic acid molecule of the invention to hybridize to at least approximately 6, 12, 20, 30, 40, 50, 60, 70, 80, 90, 100, 110, 120, 130 or 140 consecutive nucleotides of either strand of an SR-BI gene.

"SR-BI" or "SR-BI receptor" refers to a class B scavenger receptor that has been shown to bind HDL cholesterol and mediate uptake into cells (Acton, S. et al., *Science* 271:518–520). SR-BI has also been shown to bind with high affinity to modified protein (e.g. acetylated LDL, oxidized LDL, maleylated bovine serum albumin) and native LDL (Acton, et al., (1994) *J. Biochem.* 269:21003–21009). Further, SR-BI has been shown to bind anionic phospholipids, such as phosphatidylserine and phosphatidylinositol, but not zwitterionic phospholipids, such as phosphatidylcholine, phosphatidylethanolamine and sphingomyelin. Competition studies suggest that anionic phospholipids bind to SR-BI at a site close to or identical with the sites of native and modified LDL binding and that the interaction may involve polyvalent binding via multiple anionic phospholipid molecules (Rigotti, A., S. Acton and M. Krieger (1995) *J. Biochem* 270:16221–16224). SR-BI has also been shown to bind to negatively charged liposomes and apoptotic cells. The human SR-BI protein is described in Calvo et al. (1993) J. Biol. Chem. 268:18929 and hamster SR-BI is described in International Patent Application Number WO 96/00288 entitled "Class B1 and C1 Scavenger Receptors" by Acton, S. et al.

As used herein, the term "transfection" means the introduction of a nucleic acid, e.g., an expression vector, into a recipient cell by nucleic acid-mediated gene transfer. The term "transduction" is generally used herein when the transfection with a nucleic acid is by viral delivery of the nucleic acid. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of a naturally-occurring form of the recombinant protein is disrupted.

As used herein, the term "transgene" refers to a nucleic acid sequence which has been introduced into a cell. Daughter cells deriving from a cell in which a transgene has been introduced are also said to contain the transgene (unless it has been deleted). A transgene can encode, e.g., a polypeptide, or an antisense transcript, partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). Alternatively, a transgene can also be present in an episome. A transgene can include one or more transcriptional regulatory sequence and any other nucleic acid, (e.g. intron), that may be necessary for optimal expression of a selected nucleic acid.

A "transgenic animal" refers to any animal, preferably a non-human animal, e.g. a mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of a protein, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques.

The term "treating" as used herein is intended to encompass curing as well as ameliorating at least one symptom of the condition or disease.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes. Probes and Primers for Use According to the Present Invention In a preferred embodiment of the invention, the methods and kits use probes or primers. Primers of the invention refer to nucleic acids which hybridize to a nucleic acid sequence which is adjacent to the region of interest or which covers the region of interest and is extended. A primer can be used alone in a detection method, or a primer can be used together with at least one other primer or probe in a detection method. Primers can also be used to amplify at least a portion of a nucleic acid. Probes of the invention refer to nucleic acids which hybridize to the region of interest and which are not further extended. For example, a probe is a nucleic acid which hybridizes to a polymorphic region of an SR-BI gene, and which by hybridization or absence of hybridization to the DNA of a subject will be indicative of the identity of the allelic variant of the polymorphic region of the SR-BI gene. Probes or primers can be single stranded DNA (e.g., an oligonucleotide), double stranded DNA (e.g., double stranded oligonucleotide) or RNA.

Numerous procedures for determining the nucleotide sequence of a nucleic acid, or for determining the presence of mutations in nucleic acids include a nucleic acid amplification step, which can be carried out by, e.g., polymerase chain reaction (PCR). Accordingly, in one embodiment, the invention provides primers for amplifying a portion of an SR-BI gene comprising a polymorphic region of which specific allelic variants are associated with a body mass disorder. In a preferred embodiment, the portion of the human SR-BI gene will be amplified to, e.g., detect which allelic variant of a polymorphic region is present in the SR-BI gene of a subject. Preferred primers comprise a nucleotide sequence complementary to an SR-BI intronic sequence or a specific allelic variant of a polymorphic region and of sufficient length to selectively hybridize with an SR-BI gene. In a preferred embodiment, the primer, e.g., a substantially purified oligonucleotide, comprises a region having a nucleotide sequence which hybridizes under stringent conditions to about 6, 8, 10, or 12, preferably 25, 30, 40, 50, or 75 consecutive nucleotides of an SR-BI gene. In an even more preferred embodiment, the primer is capable of hybridizing to an intronic sequence and has a nucleotide sequence of an intron shown in FIG. 2 or set forth in any of SEQ ID Nos. 1–74, complements thereof, allelic variants thereof, or complements of allelic variants thereof. For example, primers comprising a nucleotide sequence of at least about 15 consecutive nucleotides, at least about 20 nucleotides or having from about 15 to about 25 nucleotides shown in FIG. 2 or set forth in any of SEQ ID Nos. 1–74 or complement thereof are provided by the invention. Primers having a sequence of more than about 25 nucleotides are also within the scope of the invention. Preferred primers of the invention are primers that can be used in PCR for amplifying the region of intron 5 comprising nucleotide 54. Even more preferred primers of the invention have the nucleotide sequence set forth in any of SEQ ID Nos.49 and 50 (see Table III).

Primers can be complementary to nucleotide sequences located close to each other or further apart, depending on the use of the amplified DNA. For example, primers can be chosen such that they amplify DNA fragments of at least about 10 nucleotides or as much as several kilobases. Preferably, the primers of the invention will hybridize selectively to nucleotide sequences located about 150 to about 350 nucleotides apart.

For amplifying at least a portion of a nucleic acid, a forward primer (i.e., 5' primer) and a reverse primer (i.e., 3' primer) will preferably be used. Forward and reverse primers hybridize to complementary stands of a double stranded nucleic acid, such that upon extension from each primer, a double stranded nucleic acid is amplified. A forward primer can be a primer having a nucleotide sequence or a portion of the nucleotide sequence shown in FIG. 2 or in SEQ ID Nos. 1–40 and 65. A reverse primer can be a primer having a nucleotide sequence or a portion of the nucleotide sequence that is complementary to a nucleotide sequence shown in FIG. 2 or in SEQ ID Nos. 1–40 and 65. Preferred forward primers comprise a nucleotide sequence set forth in SEQ ID Nos. 41, 43, 45, 47, 49, 51, 53, 55, 57, 59, 61, and 63 (shown in Table III). Preferred reverse primers comprise a nucleotide sequence set forth in SEQ ID Nos. 42, 44, 46, 48, 50, 52, 54, 56, 58, 60, 62, and 64. Preferred pairs of primers for amplifying each of the exons of human SR-BI are set forth in Table III.

Yet other preferred primers of the invention are nucleic acids which are capable of selectively hybridizing to an allelic variant of a polymorphic region of an SR-BI gene. Thus, such primers can be specific for any SR-BI gene sequence, provided that they have a nucleotide sequence which is capable of hybridizing to an SR-BI gene. Preferred primers are capable of specifically hybridizing to an allelic variant in which nucleotide 54 of intron 5 is a thymidine, e.g., a nucleic acid having SEQ ID NO. 65. Such primers can be used, e.g., in sequence specific oligonucleotide priming as described further herein.

The SR-BI nucleic acids of the invention can also be used as probes, e.g. in therapeutic and diagnostic assays. For instance, the present invention provides a probe comprising a substantially purified oligonucleotide, which oligonucleotide comprises a region having a nucleotide sequence that hybridizes under stringent conditions to at least approximately 6, 8, 10 or 12, preferably about 25, 30, 40, 50 or 75 consecutive nucleotides of an SR-BI gene. In one embodiment, the probes preferably hybridize to an intronic sequence of an SR-BI gene, e.g., an intronic sequence set forth in SEQ ID NO. 26, allelic variants thereof, complements thereof or complements of allelic variants thereof. In another embodiment, the probes are capable of hybridizing to a nucleotide sequence encompassing an intron/exon border of an SR-BI gene.

Other preferred probes of the invention are capable of hybridizing specifically to a region of an SR-BI gene which is polymorphic. In an even more preferred embodiment of the invention, the probes are capable of hybridizing specifically to one allelic variant of an SR-BI gene having a nucleotide sequence which differs from the nucleotide sequence set forth in SEQ ID NO. 1 or 3. Such probes can then be used to specifically detect which allelic variant of a polymorphic region of an SR-BI gene is present in a subject. Preferred probes of the invention are capable of hybridizing specifically to a region overlapping nucleotide 54 of intron 5 of the human SR-BI gene. In one embodiment, the probe overlapping nucleotide 54 of intron 5 is capable of hybridizing specifically to a nucleotide sequence wherein nucleotide 54 is a cytidine (as shown in FIG. 2 and set forth in SEQ ID NOs. 9 and 26). Examples of such probes include a probe having the nucleotide sequence 5' AGCCATGGC-CGGGCCCACCCT 3' (SEQ ID NO. 66); 5' CGAGCAGC-CATGGCCGGGCCCACCCTCCCCT 3' (SEQ ID NO. 67); and probes having the complement of these nucleotide sequences, i.e., 5' AGGGTGGGCCCGGCCATGGCT 3' (SEQ ID NO. 68); 5' AGGGGAGGGTGGGCCCGGC-CATGGCTGCTCG 3' (SEQ ID NO. 69). In another embodiment, the probe overlapping nucleotide 54 of intron 5 is capable of specifically hybridizing to a nucleotide sequence wherein nucleotide 54 is a thymidine (as shown in SEQ ID NO. 65). Examples of such probes include a probe having the nucleotide sequence 5' AGCCATGGCCAGGC-CCACCCT 3' (SEQ ID NO. 70); 5' CGAGCAGCCATG-GCCAGGCCCACCCTCCCCT 3' (SEQ ID NO. 71); and probes having the complement of these nucleotide sequences, i.e., 5' AGGGTGGGCCTGGCCATGGCT 3' (SEQ ID NO. 72); 5' AGGGGAGGGTGGGCCTGGC-CATGGCTGCTCG 3' (SEQ ID NO. 73). The nucleotides in bold are represent the nucleotide polymorphism.

Preferred probes of the invention have a number of nucleotides sufficient to allow specific hybridization to the target nucleotide sequence. Where the target nucleotide sequence is present in a large fragment of DNA, such as a genomic DNA fragment of several tens or hundreds of kilobases, the size of the probe may have to be longer to provide sufficiently specific hybridization, as compared to a probe which is used to detect a target sequence which is present in a shorter fragment of DNA. For example, in some diagnostic methods, a portion of an SR-BI gene may first be amplified and thus isolated from the rest of the chromosomal DNA and then hybridized to a probe. In such a situation, a shorter probe will likely provide sufficient specificity of hybridization. For example, a probe having a nucleotide sequence of about 10 nucleotides may be sufficient.

In preferred embodiments, the probe or primer further comprises a label attached thereto, which, e.g., is capable of being detected, e.g. the label group is selected from amongst radioisotopes, fluorescent compounds, enzymes, and enzyme co-factors.

In a preferred embodiment of the invention, the probe or primer is modified, such as to become more stable. Exemplary nucleic acid molecules which are modified include phosphoramidate, phosphothioate and methylphosphonate analogs of DNA (see also U.S. Pat. Nos. 5,176,996; 5,264, 564; and 5,256,775).

The probes and primers can also be modified at the base moiety, sugar moiety, or phosphate backbone, for example, to improve stability of the molecule. The probes or primers may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the nucleic acid of the invention may be conjugated to another molecule, e.g., a peptide, hybridization triggered cross-linking agent, transport agent, hybridization-triggered cleavage agent, etc.

The probes and primers may comprise at least one modified base moiety which is selected from the group including but not limited to 5-fluorouracil, 5-bromouracil, 5-chlorouracil, 5-iodouracil, hypoxanthine, xantine, 4-acetylcytidine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytidine, 5-methylcytidine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytidine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The probes and primers may also comprise at least one modified sugar moiety selected from the group including but not limited to arabinose, 2-fluoroarabinose, xylulose, and hexose.

In yet another embodiment, the probe or primer comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the probe or primer is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330).

Any probe or primer of the invention can be prepared according to methods well known in the art and described, e.g., in Sambrook, J. Fritsch, E. F., and Maniatis, T. (1989) Molecular Cloning: A Laboratory Manual, Cold Spring Harbor Laboratory Press, Cold Spring Harbor, N.Y. For example, discrete fragments of the DNA can be prepared and cloned using restriction enzymes. Alternatively, probes and primers can be prepared using the Polymerase Chain Reaction (PCR) using primers having an appropriate sequence.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

Kits

As set forth herein, the invention provides methods, e.g., diagnostic and therapeutic methods, e.g., for determining the identity of the allelic variant of a polymorphic region present in an SR-BI gene, wherein specific allelic variants of the polymorphic region are associated with body mass disorders. In a preferred embodiment, the kit can be used to determine whether a subject is at risk of developing an abnormal body mass index. The kit of the invention can also be used to determine if a subject who is obese carries an SR-BI allele associated with a high body mass. This information could then be used, e.g., to optimize treatment of such obese individuals.

In preferred embodiments, the kit comprises a probe or primer which is capable of hybridizing to an SR-BI gene and thereby identifying whether the SR-BI gene contains an allelic variant of a polymorphic region which is associated with the body mass disorder. The kit preferably further comprises instructions for use in diagnosing a subject as having, or having a predisposition, towards developing a body mass disorder. In preferred embodiments, the body mass disorder is an abnormally high body mass. The probe or primers of the kit can be any of the probes or primers described in the above section.

Preferred kits for amplifying a region of an SR-BI gene comprising a polymorphic region of interest comprise two primers. In one embodiment, at least one primer is capable of hybridizing to an SR-BI intronic sequence. A preferred kit comprises a primer having SEQ ID NO. 49 and a primer having SEQ ID NO. 50.

The kits of the invention can also comprise one or more control nucleic acid or reference nucleic acid, such as nucleic acids comprising an SR-BI intronic sequence. For example, a kit can comprise primers for amplifying a polymorphic region of an SR-BI gene and a control DNA corresponding to such an amplified DNA and having the nucleotide sequence of a specific allelic variant. Thus, direct comparison can be performed between the DNA amplified from a subject and the DNA having the nucleotide sequence of a specific allelic variant.

Yet other kits of the invention comprise at least one reagent necessary to perform the assay. For example, the kit can comprise an enzyme. Alternatively the kit can comprise a buffer or any other necessary reagent.

Diagnostic and Prognostic Assays

The present invention provides methods for determining the molecular structure of at least one polymorphic region of an SR-BI gene, specific allelic variants of said polymorphic region being associated with body mass disorders, e.g., an abnormally high body mass, obesity. In one embodiment, determining the molecular structure of a polymorphic region of an SR-BI gene comprises determining the identity of the allelic variant. A polymorphic region of an SR-BI gene, of which specific alleles are associated with body mass disorders can be located in an exon, an intron, at an intron/exon border, or in the promoter of the SR-BI gene.

The invention provides methods for determining whether a subject has, or is at risk, of developing a body mass disorder. In fact, the presence of a thymidine at position 54 of intron 5 has been associated with a high body mass (see Examples). Such disorders can be associated with an aberrant SR-BI activity, e.g., abnormal binding to a form of a lipid, or an aberrant SR-BI protein level. An aberrant SR-BI protein level can result from an aberrant transcription or post-transcriptional regulation. Thus, allelic differences in specific regions of an SR-BI gene can result in differences of SR-BI protein due to differences in regulation of expression. In particular, some of the identified polymorphisms in the human SR-BI gene may be associated with differences in the level of transcription, RNA maturation, splicing, or translation of the SR-BI gene or transcription product.

In preferred embodiments, the methods of the invention can be characterized as comprising detecting, in a sample of cells from the subject, the presence or absence of a specific allelic variant of one or more polymorphic regions of an SR-BI gene. The allelic differences can be: (i) a difference in the identity of at least one nucleotide or (ii) a difference in the number of nucleotides, which difference can be a single nucleotide or several nucleotides. The invention also provides methods for detecting differences in SR-BI genes such as chromosomal rearrangements, e.g., chromosomal dislocation.

A preferred detection method is allele specific hybridization using probes overlapping the polymorphic site and having about 5, 10, 20, 25, or 30 nucleotides around the polymorphic region. Examples of probes for detecting specific allelic variants of the polymorphic region located in intron 5 are probes comprising a nucleotide sequence set forth in any of SEQ ID NO. 75–82. In a preferred embodiment of the invention, several probes capable of hybridizing specifically to allelic variants are attached to a solid phase support, e.g., a "chip". Oligonucleotides can be bound to a solid support by a variety of processes, including lithography. For example a chip can hold up to 250,000 oligonucleotides (GeneChip, Affymetrix). Mutation detection analysis using these chips comprising oligonucleotides, also termed "DNA probe arrays" is described e.g., in Cronin et al. (1996) Human Mutation 7:244 and in Kozal et al. (1996) Nature Medicine 2:753. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment. For example, the identity of the allelic variant of the nucleotide polymorphism of nucleotide 54 of intron 5 and that of other possible polymorphic regions can be determined in a single hybridization experiment.

In other detection methods, it is necessary to first amplify at least a portion of an SR-BI gene prior to identifying the allelic variant. Amplification can be performed, e.g., by PCR and/or LCR, according to methods known in the art. In one embodiment, genomic DNA of a cell is exposed to two PCR primers and amplification for a number of cycles sufficient to produce the required amount of amplified DNA. In preferred embodiments, the primers are located between 150 and 350 base pairs apart. Preferred primers, such as primers for amplifying each of the exons of the human SR-BI gene, are listed in Table III in the Examples. Details regarding the PCR reaction are indicated in Table IV, also in the Examples.

Alternative amplification methods include: self sustained sequence replication (Guatelli, J. C. et al., 1990, Proc. Natl. Acad. Sci. U.S.A. 87:1874–1878), transcriptional amplification system (Kwoh, D. Y. et al., 1989, Proc. Natl. Acad. Sci. U.S.A. 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment, any of a variety of sequencing reactions known in the art can be used to directly sequence at least a portion of an SR-BI gene and detect allelic variants, e.g., mutations, by comparing the sequence of the sample sequence with the corresponding wild-type (control) sequence. Exemplary sequencing reactions include those based on techniques developed by Maxam and Gilbert (*Proc. Natl Acad Sci USA* (1977) 74:560) or Sanger (Sanger et al (1977) *Proc. Nat. Acad. Sci* 74:5463). It is also contemplated that any of a variety of automated sequencing procedures may be utilized when performing the subject assays (*Biotechniques* (1995) 19:448), including sequencing by mass spectrometry (see, for example, U.S. Pat. No. 5,547,835 and international patent application Publication Number WO 94/16101, entitled *DNA Sequencing by Mass Spectrometry* by H. Köster; U.S. Pat. No. 5,547,835 and international patent application Publication Number WO 94/21822 entitled "DNA Sequencing by Mass Spectrometry Via Exonuclease Degradation" by H. Köster), and U.S. Pat. No. 5,605,798 and International Patent Application No. PCT/US96/03651 entitled *DNA Diagnostics Based on Mass Spectrometry* by H. Köster; Cohen et al. (1996) *Adv Chromatogr* 36:127–162; and Griffin et al. (1993) *Appl Biochem Biotechnol* 38:147–159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732 entitled "Method of DNA sequencing employing a mixed DNA-polymer chain probe" and U.S. Pat. No. 5,571,676 entitled "Method for mismatch-directed in vitro DNA sequencing".

In some cases, the presence of a specific allele of an SR-BI gene in DNA from a subject can be shown by restriction enzyme analysis. For example, a specific nucleotide polymorphism can result in a nucleotide sequence comprising a restriction site which is absent from the nucleotide sequence of another allelic variant. In particular, the presence of a cytidine at position 54 of intron 5 creates an ApaI site, whereas the presence of a thymidine, associated with high body mass, at this position destroys the ApaI site.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (Myers, et al. (1985) *Science* 230:1242). In general, the technique of "mismatch cleavage" starts by providing heteroduplexes formed by hybridizing a control nucleic acid, which is optionally labeled, e.g., RNA or DNA, comprising a nucleotide sequence of an SR-BI allelic variant with a sample nucleic acid, e.g, RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, Cotton et al (1988) *Proc. Natl Acad Sci USA* 85:4397; Saleeba et al (1992) Methods Enzymod. 217:286–295. In a preferred embodiment, the control or sample nucleic acid is labeled for detection.

In other embodiments, alterations in electrophoretic mobility is used to identify the type of SR-BI allelic variant. For example, single strand conformation polymorphism (SSCP) may be used to detect differences in electrophoretic mobility between mutant and wild type nucleic acids (Orita et al. (1989) *Proc Natl. Acad. Sci USA* 86:2766, see also Cotton (1993) *Mutat Res* 285:125–144; and Hayashi (1992) *Genet Anal Tech Appl* 9:73–79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the identity of an allelic variant of a polymorphic region is obtained by analyzing the movement of a nucleic acid comprising the polymorphic region in polyacrylamide gels containing a gradient of denaturant is assayed using denaturing gradient gel electrophoresis (DGGE) (Myers et al (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:1275).

Examples of techniques for detecting differences of at least one nucleotide between 2 nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) *Nature* 324:163); Saiki et al (1989) *Proc. Natl Acad. Sci USA* 86:6230; and Wallace et al. (1979) Nucl. Acids Res. 6:3543). Such allele specific oligonucleotide hybridization techniques may be used for the simultaneous detection of several nucleotide changes in different polymorphic regions of SR-BI. For example, oligonucleotides having nucleotide sequences of specific allelic variants are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238; Newton et al. (1989) Nucl. Acids Res. 17:2503). This technique is also termed "PROBE" for Probe Oligo Base Extension. In addition it may be desirable to introduce a novel restriction site in the region of the mutation to create cleavage-based detection (Gasparini et al (1992) *Mol. Cell Probes* 6:1).

In another embodiment, identification of the allelic variant is carried out using an oligonucleotide ligation assay (OLA), as described, e.g., in U.S. Pat. No. 4,998,617 and in Landegren, U. et al., Science 241:1077–1080 (1988). The OLA protocol uses two oligonucleotides which are designed to be capable of hybridizing to abutting sequences of a single strand of a target. One of the oligonucleotides is linked to a separation marker, e.g,. biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., Proc. Natl. Acad. Sci. (U.S.A.) 87:8923–8927 (1990). In this method, PCR is used to achieve the exponential amplification of target DNA, which is then detected using OLA.

Several techniques based on this OLA method have been developed and can be used to detect specific allelic variants of a polymorphic region of an SR-BI gene. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996)Nucleic Acids Res 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

The invention further provides methods for detecting single nucleotide polymorphisms in an SR-BI gene. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms.

In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA TM is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779–7784 (1989); Sokolov, B. P., Nucl. Acids Res. 18:3671 (1990); Syvanen, A. -C., et al., Genomics 8:684–692 (1990), Kuppuswamy, M. N. et al., Proc. Natl. Acad. Sci. (U.S.A.) 88:1143–1147 (1991); Prezant, T. R. et al., Hum. Mutat. 1:159–164 (1992); Ugozzoli, L. et al., GATA 9:107–112 (1992); Nyren, P. et al., Anal. Biochem. 208:171–175 (1993)). These methods differ from GBA TM in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., Amer. J. Hum. Genet. 52:46–59 (1993)).

For determining the identity of the allelic variant of a polymorphic region located in the coding region of an SR-BI gene, yet other methods than those described above can be used. For example, identification of an allelic variant which encodes a mutated SR-BI protein can be performed by using an antibody specifically recognizing the mutant protein in, e.g., immunohistochemistry or immunoprecipitation. Antibodies to wild-type SR-BI protein are described, e.g, in Acton et al. (1999) Science 271:518 (anti-mouse SR-BI antibody cross-reactive with human SR-BI). Other antibodies to wild-type SR-BI or mutated forms of SR-BI proteins can be prepared according to methods known in the art. Alternatively, one can also measure an activity of an SR-BI protein, such as binding to a lipid or lipoprotein. Binding assays are known in the art and involve, e.g., obtaining cells from a subject, and performing binding experiments with a labeled lipid, to determine whether binding to the mutated form of the receptor differs from binding to the wild-type of the receptor.

If a polymorphic region is located in an exon, either in a coding or non-coding region of the gene, the identity of the allelic variant can be determined by determining the molecular structure of the mRNA, pre-mRNA, or cDNA. The molecular structure can be determined using any of the above described methods for determining the molecular structure of the genomic DNA, e.g., sequencing and SSCP.

The methods described herein may be performed, for example, by utilizing pre-packaged diagnostic kits, such as those described above, comprising at least one probe or primer nucleic acid described herein, which may be conveniently used, e.g., to determine whether a subject has or is at risk of developing a disease associated with a specific SR-BI allelic variant.

Sample nucleic acid for using in the above-described diagnostic and prognostic methods can be obtained from any cell type or tissue of a subject. For example, a subject's bodily fluid (e.g. blood) can be obtained by known techniques (e.g. venipuncture). Alternatively, nucleic acid tests can be performed on dry samples (e.g. hair or skin). Fetal nucleic acid samples for prenatal diagnostics can be obtained from maternal blood as described in International Patent Application No. WO91/07660 to Bianchi. Alternatively, amniocytes or chorionic villi may be obtained for performing prenatal testing.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, New York).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Methods of Treatment of Diseases or Disorders

The invention further provides methods of treating subjects having a disease or disorder associated with a specific allelic variant of a polymorphic region of an SR-BI gene, e.g., a disorder associated with an abnormal body mass, e.g., obesity. In one embodiment, the method comprises (a) determining the identity of the allelic variant; and (b) administering to the subject a compound that compensates for the effect of the specific allelic variant. The polymorphic region can be localized at any location of the gene, e.g., in the promoter (e.g., in a regulatory element of the promoter), in an exon, (e.g., coding region of an exon), in an intron, or at an exon/intron border. Thus, depending on the site of the polymorphism in the SR-BI gene, a subject having a specific variant of the polymorphic region which is associated with a specific disease or condition, can be treated with compounds which specifically compensate for the allelic variant.

For example, the allelic variant can be a mutant allele, i.e., an allele which when present in one, or preferably two copies, in a subject results in a change in the phenotype of the subject. A mutation can be a substitution, deletion, and/or addition of at least one nucleotide relative to the wild-type allele. Depending on where the mutation is located in the SR-BI gene, the subject can be treated to specifically compensate for the mutation. For example, if the mutation is present in the coding region of the gene and results in an inactive or less active SR-BI protein, the subject can be treated, e.g., by administration to the subject of a nucleic acid encoding a wild-type SR-BI protein, such that the expression of the wild-type SR-BI protein compensates for the endogenous mutated form of the SR-BI protein. Nucleic acids encoding wild-type human SR-BI protein are described, e.g., in Calvo and Vega (1993) J. Biol. Chem. 268:18929.

In one embodiment, the invention provides a method for predicting whether a subject is susceptible of developing an abnormal body mass, e.g, a high body mass. According to the method of the invention, a subject is tested for the presence of a nucleotide other than a cytidine at position 54 of intron 5 of human SR-BI and where the subject has such a nucleotide, the subject can be put on a diet to prevent the increase in body mass.

Furthermore, depending on the site of the mutation in the SR-BI protein and the specific effect on its activity, specific treatments can be designed to compensate for that effect. The SR-BI protein is a cell surface receptor which binds specific forms of lipids, e.g., modified lipid or lipoproteins, e.g., HDL. Thus, an SR-BI protein has an extracellular domain which binds specific molecules, e.g., lipids, a transmembrane domain, and an intracellular domain, which is likely to transmit an intracellular signal. The structure of SR-BI proteins is further described, e.g., in Calvo and Vega, supra; Acton et al. (1994) J. Biol. Chem. 269:21003; Acton et al. (1995) Science 271:518; Rigotti et al. (1995) J. Biol. Chem. 270:16221; Fukasawa et al. (1996) Exp. Cell. Res. 222:246; Wang et al. (1996) J. Biol. Chem. 271:21001; and published PCT Application having publication number WO 96/00288 by Acton et al. Thus, if the mutation results in an SR-BI protein which is less capable of binding certain types of modified lipids, resulting in an accumulation of such lipids in the subject, a treatment can be designed which removes such modified lipids from the subject. In one embodiment, a compound which binds this form of lipid and is capable of targeting the lipid to a site where it is eliminated, is administered to the subject. Alternatively, the expression of another cell surface receptor which binds this type of lipid can be increased. In fact, both SR-BI and the class B scavenger receptor CD36 are capable of interacting with anionic phospholipids (Rigotti et al., supra). Thus, if a subject has a mutant SR-BI protein which is defective in its binding to anionic phospholipids, the subject can be treated by administration of a compound which increases CD36 protein levels in the cells.

In situations in which the mutant SR-BI protein binds certain forms of lipids with higher affinity, and if this is causing or contributing to a disease, a subject having such a mutated SR-BI protein can be treated, e.g., by administration of compounds which inhibit or decrease the interaction between the specific form of the lipid and SR-BI. For example, soluble forms of SR-BI proteins or binding fragments thereof, can be administered to the subject. Alternatively, small molecules can be administered to the subject for interfering in the interaction between SR-BI and a lipid.

A mutant SR-BI protein can also be an SR-BI protein having a mutation in the cytoplasmic domain of the protein which results in an aberrant signal transduction from the receptor. Subjects having such a mutation can be treated, e.g., by administration of compounds which induce the same or similar signal transduction or compounds which act downstream of the receptor.

The effect of a mutation in an SR-BI protein can be determined according to methods known in the art. For example, if the mutation is located in the extracellular portion of the protein, one can perform binding assays with specific forms of lipids, e.g., HDL, and determine whether the binding affinity of such lipid with the mutated SR-BI protein is different from the binding affinity of the lipid with the wild-type protein. Such assays can be performed using a soluble form of an SR-BI protein or a membrane bound form of the protein. If the mutation in the SR-BI protein is located in the cytoplasmic domain of the protein, signal transduction experiments can be performed to determine whether the signal transduced from the mutated receptor differs from the signal transduced from the wild-type receptor. Alternatively, one can also investigate whether binding to a protein which interacts with the cytoplasmic domain of the receptor is affected by the mutation. Such determination can be made by, e.g., by immunoprecipitation.

Yet in another embodiment, the invention provides methods for treating a subject having a mutated SR-BI gene, in which the mutation is located in a regulatory region of the gene. Such a regulatory region can be localized in the promoter of the gene, in the 5' or 3' untranslated region of an exon, or in an intron. A mutation in a regulatory region can result in increased production of SR-BI protein, decreased production of SR-BI protein, or production of SR-BI having an aberrant tissue distribution. The effect of a mutation in a regulatory region upon the SR-BI protein can be determined, e.g., by measuring the SR-BI protein level or mRNA level in cells having an SR-BI gene having this mutation and which, normally (i.e., in the absence of the mutation) produce SR-BI protein. The effect of a mutation can also be determined in vitro. For example, if the mutation is in the promoter, a reporter construct can be constructed which comprises the mutated promoter linked to a reporter gene, the construct transfected into cells, and comparison of the level of expression of the reporter gene under the control of the mutated promoter and under the control of a wild-type promoter. Such experiments can also be carried out in mice transgenic for the mutated promoter. If the mutation is located in an intron, the effect of the mutation can be determined, e.g., by producing transgenic animals in which the mutated SR-BI gene has been introduced and in which the wild-type gene may have been knocked out. Comparison of the level of expression of SR-BI in the mice transgenic for the mutant human SR-BI gene with mice transgenic for a wild-type human SR-BI gene will reveal whether the mutation results in increased, decreased synthesis of the SR-BI protein and/or aberrant tissue distribution of SR-BI protein. Such analysis could also be performed in cultured cells, in which the human mutant SR-BI gene is introduced and, e.g., replaces the endogenous wild-type SR-BI gene in the cell. Thus, depending on the effect of the mutation in a regulatory region of an SR-BI gene, a specific treatment can be administered to a subject having such a mutation. Accordingly, if the mutation results in decreased production of an SR-BI protein, the subject can be treated by administration of a compound which increases synthesis, such as by increasing SR-BI gene expression, and wherein the compound acts at a regulatory element different from the one which is mutated. Alternatively, if the mutation results in increased SR-BI protein levels, the subject can be treated by administration of a compound which reduces SR-BI protein production, e.g., by reducing SR-BI gene expression or a compound which inhibits or reduces the activity of SR-BI.

Furthermore, it is likely that subjects having different allelic variants of an SR-BI polymorphic region will respond differently to therapeutic drugs to treat diseases or conditions, such as those associated with an abnormal lipid level. Cholesterol-lowering drugs include lovastatin (MEVACOR; Merck & Co.), simvastatin (ZOCOR; Merck & Co.), dextrothyroxine (CHOLOXIN; Knoll Pharmaceutical Co.), pamaqueside (Pfizer), cholestryramine (QUESTRAN; Bristol-Myers Squibb), colestipol (COLESTID; Pharmacia & Upjohn), acipomox (Pharmacia & Upjohn), fenofibrate (LIPIDIL), gemfibrozil (LOPID; Warner-Lambert), cerivastatin (LIPOBAY, Bayer), fluvastatin (LESCOL; Novartis), atorvastatin (LIPITOR, Warner-Lambert), etofylline clofibrate (DUOLIP; Merckle (Germany)), probucol (LORELCO; Hoechst Marion Roussel), omacor (Pronova (Norway), etofibrate (Merz (Germany), clofibrate (ATROMID-S; Wyeth-Ayerst (AHP)), and niacin (numerous manufacturers). Drugs for treating obesity and/or gallstones include dexfenfluramine (REDUX, Interneuron Pharmaceuticals), megestrol acetate (MEGACE, Bristol-Myers Squibb), Phenylpropanolamine (ACUTRIM; Ciba; and DEXUTRIM; Thompson), fluoxetine (PROZAC, Lilly), dextroamphetamine (DEXEDRINE, SmithKline Beecham), fenfluramine and phentermine, chenodiol (CHENIX, Solvay), orlistat (XENICAL, Roche), anandamide (Yissum (Israel)), PCM-4 (Omega Pharmaceutical), mono-octanoin (MOCTAN, Stokely-van Camp), sibutramine (MERIDIA, Knoll), testosterone (TESTODERM, Alza), oxandrolone (OXANDRIN, Bio-Technology General), ceruletide diethylamine (TYMTRAN, Pharmacia & Upjohn), testosterone and dihydrotestosterone (ANDROGEL and ANDROGEL-DHT, unimed), somatropin (SEROSTIM, Ares-Serono and BIO-TROPIN, Biotechnology General), and thalidomide (SYNOVIR, Celgene).

A correlation between drug responses and specific alleles of SR-BI can be shown, for example, by clinical studies wherein the response to specific drugs of subjects having different allelic variants of a polymorphic region of an SR-BI gene is compared. Such studies can also be performed using animal models, such as mice having various alleles of human SR-BI genes and in which, e.g., the endogenous SR-BI has been inactivated such as by a knock-out mutation. Test drugs are then administered to the mice having different human SR-BI alleles and the response of the different mice to a specific compound is compared. Accordingly, the invention provides assays for identifying the drug which will be best suited for treating a specific disease or condition in a subject. For example, it will be possible to select drugs which will be devoid of toxicity, or have the lowest level of toxicity possible for treating a subject having a disease or condition, e.g., obesity.

Other Uses for the Nucleic Acids of the Invention

The identification of different alleles of SR-BI can also be used for purposes of identifying an individual among other individuals from the same species. For example, DNA sequences can be used as a fingerprint for detection of different individuals within the same species (Thompson, J. S. and Thompson, eds., Genetics in Medicine, WB Saunders Co., Philadelphia, Pa. (1991)). This is useful, e.g., in forensic studies.

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., New York); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

5. EXAMPLES

The invention now being generally described, it will be more readily understood by reference to the following examples which are included merely for purposes of illustration of certain aspects and embodiments of the present invention, and are not intended to limit the invention.

Example 1

Identification of a Polymorphism in Intron 5 of the Human SR-BI Gene Which is Associated with a High Body Mass Index This example describes the identification of a polymorphism in the human SR-BI gene using the method of single stranded conformation polymorphism (SSCP).

The subjects used in this study were 142 Caucasian men and women born and living in Spain. The age range was between 15 and 75 years with a mean value of 42 years. They were not selected on the basis of any preselected disease. These individuals had a known HDL level (normal, high, or low), known triglyceride level, and known body mass index. Plasma lipid parameters as well as anthropometric and behavioral factors were determined in these subjects.

Genomic DNA from the subjects was subjected to PCR in 25 µl reactions (1× PCR Amplitaq polymerase buffer, 0.1 mM dNTPs, 0.8 µM 5' primer, 0.8 µM 3' primer, 0.75 units of Amplitaq polymerase, 50 ng genomic DNA) using described pairs of primers set forth in Table III for amplifying each of the 12 exons under the following cycle conditions: 94° C. for 2 min, 35×[94° C. for 40 sec, annealing temp for 30 sec, 72° C. for 1 min], 72° C. 5 min, 4° C. hold. The optimum PCR annealing temperatures for each set of primers are given in Table IV. The expected sizes of the PCR products, as well as diagnostic restriction sites, are also indicated in Table IV.

TABLE III

| exon | primer name | SEQ ID NO. | Nucleotide Sequence (5' -> 3') |
|---|---|---|---|
| 1 | 5e16srb1 | 41 | CCCCTGCCGCCGGAATCCTGAAG |
|   | 3e16srb1 | 42 | CGCTTTGGCGGAGCAGCCCATGTC |
| 2 | 5e22srb1 | 43 | TGGGGCCCTCATCACTCTCCTCAC |
|   | 3e22srb1 | 44 | GCAGCCTCCCCATCCCGTCCACT |
| 3 | 5e30srb1 | 45 | ATTGCAGGCGAGTAGAAG |
|   | 3e30srb1 | 46 | CAGGCGGGAGGAGAGACA |
| 4 | 5e41srb1 | 47 | TGGGCTCTTTGCTGTGAGGC |
|   | 3e41srb1 | 48 | CCAGGCTGTGTGAGGGGAAG |
| 5 | 5e50srb1 | 49 | GCCCAGAATGTTCAGACCAG |
|   | 3e50srb1 | 50 | GCACCCTCTTCACGACAAAG |
| 6 | 5e60srb1 | 51 | CACCTGAGAGGGCTTATTA |
|   | 3e60srb1 | 52 | CAAAATGCTTTCCAAGTGC |
| 7 | 5e71srb1 | 53 | GCCGCCGGGTCTGGGTGTCC |
|   | 3e71srb1 | 54 | CAGAGGCCAGAGATTAAGCAGAC |
| 8 | 5e81srb1 | 55 | TTGTATGATGTCCCCTCCCT |
|   | 3e81srb1 | 56 | TTCCCACCACCCCAGCCCAC |
| 9 | 5e91srb1 | 57 | GGTTGACTGTGTCCCTGGAG |
|   | 3e91srb1 | 58 | GGGAACACTGGAGCACTGAGC |
| 10 | 5e104srb1 | 59 | GGTGGTGAGGGTTTAGTGTG |
|   | 3e104srb1 | 60 | CTCCCCCCGCCTCCTGCCTC |
| 11 | 5e112srb1 | 61 | AAGGTGTTGGGTGGCATCTG |
|   | 3e112srb1 | 62 | GGCTCCAGGCTGCGGTTGGC |
| 12 | 5e100srb1 | 63 | TTGAAGAACCGTGTAAAAC |
|   | 3e100srb1 | 64 | TTGAGGCTGAAGGAATGA |

The amplified genomic DNA fragments were then analyzed by SSCP (Orita et al. (1989) *PNAS USA* 86:2766, see also Cotton (1993) *Mutat Res* 285:125–144; and Hayashi (1992) *Genet Anal Tech Appl* 9:73–79). From each 25 µl PCR reaction, 3 µl was taken and added to 7 µl of loading buffer. The mixture was heated to 94° C. for 5 min and then immediately cooled in a slurry of ice-water. 3–4 µl were then loaded on a 10% polyacrylamide gel containing 10% glycerol and then subjected to electrophoresis either overnight at 4 Watts at room temperature, or 6 hours at 20 Watts at 4° C. The secondary structure of single-stranded nucleic acids varies according to sequence, thus allowing the detection of small differences in nucleic acid sequence between similar nucleic acids. At the end of the electrophoretic period, the DNA was analyzed by gently overlaying a mixture of dyes onto the gel (1× the manufacturer's recommended concentration of SYBR Green I and SYBR Green II in 0.5×TBE buffer (Molecular Probes)) for 5 min, followed by rinsing in distilled water and detection in a Fluoroimager 575 (Molecular Dynamics).

A polymorphism was detected in the genomic region comprising exon 5. To determine the identity of the polymorphism by SSCP, this region was reamplified using the aforementioned primers which were modified to contain additional sequence which could be used to directly sequence the PCR product (M13 forward sequence for 5' primer and M13 reverse sequence for 3' primer) on the 5' end of the primers as listed in Table III. In particular, the forward primers (5' end primers) contained the nucleotide sequence "TGTAAAACGACGGCCAGT" (SEQ ID NO. 74) located 5' of the nucleotide sequences shown in Table III and the reverse primer (3' end primer) contained the nucleotide sequence "CAGGAAACAGCTATGACC" (SEQ ID NO. 75) located 5' of the nucleotide sequence shown in Table III. The genomic DNA from the subjects was subjected to PCR in 50 µl reactions (1× PCR Amplitaq polymerase buffer, 0.1 mM dNTPs, 0.8 µM 5' primer, 0.8 µM 3' primer, 0.75 units of Amplitaq polymerase, 50 ng genomic DNA) using each of the above described pairs of primers under the following cycle conditions: 94° C. for 2 min, 35×[94° C. for 40 sec, annealing temp for 30 sec, 72° C. for 1 min], 72° C. 5 min, 4° C. hold. The optimum PCR annealing temperatures for each of the primer pairs are given in Table IV. The newly amplified products were then purified by agarose gel electrophoresis and subjected to sequencing using M13 forward and reverse primers. Table IV also indicates the size of DNA fragments obtained when digesting the amplified fragment with the restriction enzyme indicated in the table.

TABLE IV

| Exon | primer pairs | Temp. | Product length | Enzyme check |
|---|---|---|---|---|
| 1 | SEQ ID NO. 41 SEQ ID NO. 42 | 65° C. | 162 bp | BamHI (144, 118) |
| 2 | SEQ ID NO. 43 SEQ ID NO. 44 | 64° C. | 294 bp | ApaI (189, 98, 7) |
| 3 | SEQ ID NO. 45 SEQ ID NO. 46 | 57° C. | 281 bp | XhoI (153, 128) |
| 4 | SEQ ID NO. 47 SEQ ID NO. 48 | 59° C. | 360 bp | SpeI (292, 68) |
| 5 | SEQ ID NO. 49 SEQ ID NO. 50 | 57° C. | 291 bp | BamHI (157, 134) |
| 6 | SEQ ID NO. 51 SEQ ID NO. 52 | 52° C. | 273 bp | DraII (179, 72, 22) |
| 7 | SEQ ID NO. 53 SEQ ID NO. 54 | 59° C. | 290 bp | EcoRI (184, 106) |
| 8 | SEQ ID NO. 55 SEQ ID NO. 56 | 58° C. | 261 bp | HaeIII (158, 103) |
| 9 | SEQ ID NO. 57 SEQ ID NO. 58 | 57° C. | 206 bp | PstI (107, 99) |
| 10 | SEQ ID NO. 59 SEQ ID NO. 60 | 56° C. | 253 bp | AvaII (148, 105) |
| 11 | SEQ ID NO. 61 SEQ ID NO. 62 | 60° C. | 327 bp | NcoI (242, 85) |
| 12 | SEQ ID NO. 63 SEQ ID NO. 64 | 51° C. | 303 bp | PstI (184, 119) |

The results demonstrate the presence of a polymorphism in the human SR-BI gene which is located in the 5' end of the intron between exons 5 and 6 (intron 5). This polymorphism corresponds to a substitution of the cytidine at position 54 from the 5' end of intron 5 (position 1 being the first nucleotide of the intron) with a thymidine. The nucleotide substitution is found with an approximate frequency of 24% in the Spanish population studied.

Furthermore, the results indicate that this polymorphism correlates with a high body mass index in premenopausal women. Statistical analysis was carried out using the SPSS statistical program. The GLM General Factorial procedure was used. This procedure provides regression analysis and analysis of variance for one dependent variable (in this case BMI) by one or more factors (int his case intron 5 polymorphism). Using this general linear model procedure, one can test null hypotheses about the effects of other variables on the means of various groupings of a single dependent variable. One can investigate interactions between factors as well as the effects of individual factors, some of which may be random. In additions, the effects of covariates and covariate interactions (such as age) with factors can be included. Thus, use of this program indicated a correlation between the presence of thymidine at position 54 of intron 5 with a high body mass in premenopausal women.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for determining whether a human subject has, or is at risk of developing, an abnormally high body mass index, comprising determining the identity of nucleotide 54 of intron 5 of the SR-BI gene of the subject wherein the presence of a thymidine indicates that the subject has, or is at risk of developing an abnormally high body mass index.

2. A method of claim 1, wherein determining the identity of nucleotide 54 of intron 5 comprises contacting a nucleic acid of the subject with at least one probe or primer which is capable of hybridizing to an SR-BI gene.

3. A method of claim 2, wherein the probe or primer is capable of specifically hybridizing to a nucleic acid sequence comprising nucleotide 54 of intron 5.

4. A method of claim 3, wherein the probe or primer is capable of specifically hybridizing to a nucleic acid having a thymidine at position 54 of intron 5 of the SR-BI gene.

5. A method of claim 2, wherein the probe or primer has a nucleotide sequence from about 15 to about 30 nucleotides.

6. A method of claim 2, wherein the probe or primer is a single stranded nucleic acid.

7. A method of claim 2, wherein the probe or primer is labeled.

8. A method of claim 1, wherein determining the identity of nucleotide 54 of intron 5 is carried out by allele specific hybridization.

9. A method of claim 1, wherein determining the identity of nucleotide 54 of intron 5 is carried out by primer specific extension.

10. A method of claim 1, wherein determining the identity of nucleotide 54 of intron 5 is carried out by an oligonucleotide ligation assay.

11. A method of claim 1, wherein determining the identity of nucleotide 54 of intron 5 comprises performing a restriction enzyme site analysis.

12. A method of claim 11, wherein the restriction enzyme is an ApaI enzyme.

13. A method of claim 1, wherein determining the identity of nucleotide 54 of intron 5 is carried out by single-stranded conformation polymorphism.

14. A kit for determining whether a human subject has, or is at risk of developing, an abnormally high body mass index, comprising a probe or primer which is capable of specifically hybridizing to a region of a human SR-BI gene including nucleotide 54 of intron 5, wherein the presence of a thymidine at nucleotide 54 of intron 5 in the SR-BI gene of the subject indicates that the subject has, or is at risk of developing an abnormally high body mass index, and instructions for use.

15. A kit of claim 14, wherein the probe or primer is capable of hybridizing specifically to a region of the human SR-BI gene comprising a cytidine at nucleotide 54 of intron 5.

16. A kit of claim 4, wherein the probe or primer is capable of hybridizing specifically to a region of the human SR-BI gene comprising a thymidine at nucleotide 54 of intron 5.

17. A kit of claim 15, further comprising a second probe or primer which is capable of hybridizing specifically to a region of the human SR-BI gene comprising a thymidine at nucleotide 54 of intron 5.

18. A kit of claim 14, wherein the probe or primer has a nucleotide sequence from about 15 to about 30 nucleotides.

19. A kit of claim 14, wherein the probe or primer is a single stranded nucleic acid.

20. A kit of claim 14, wherein the probe or primer is labeled.

21. A method of claim 2, wherein the primer comprises a nucleotide sequence selected from the group consisting of: SEQ ID NO. 49 and SEQ ID NO. 50.

22. A method of claim 2, wherein the probe or primer is capable of hybridizing to SEQ ID NO. 9, SEQ ID NO. 26 or SEQ ID NO. 65 or the complement thereof.

23. A method of claim 2, wherein the probe or primer comprises a nucleic acid selected from the group consisting of: SEQ ID NO. 66, SEQ ID NO. 67, SEQ ID NO. 68 and SEQ ID NO. 69.

24. A method of claim 2, wherein the probe or primer comprises a nucleic acid selected from the group consisting of SEQ ID NO. 70, SEQ ID NO. 71, SEQ ID NO. 72 and SEQ ID NO. 73.

25. A kit of claim 14, wherein the probe or primer is capable of specifically hybridizing to SEQ ID NO. 9, SEQ ID NO. 26 or SEQ ID NO. 65 or the complement thereof.

26. A kit of claim 14, wherein the probe or primer comprises a nucleic acid selected from the group consisting of SEQ ID NO. 66, SEQ ID NO. 67, SEQ ID NO. 68 and SEQ ID NO. 69.

27. A kit of claim 14, wherein the probe or primer comprises a nucleic acid selected from the group consisting of: SEQ ID NO. 70, SEQ ID NO. 71, SEQ ID NO. 72 and SEQ ID NO. 73.

28. The method of claim 1, wherein the subject is a woman.

* * * * *

UNITED STATES PATENT AND TRADEMARK OFFICE
CERTIFICATE OF CORRECTION

PATENT NO. : 6,030,778
DATED : February 29, 2000
INVENTOR(S) : Susan L. Acton, et al.

Page 1 of 1

It is certified that error appears in the above-identified patent and that said Letters Patent is hereby corrected as shown below:

In column 1, before Background of the Invention, please insert the following:

Government Support

This invention was made with government support under 58-1950-9-001 awarded by the United States Department of Agriculture. The government has certain rights in the invention.

Signed and Sealed this

Twelfth Day of June, 2001

*Attest:*

*Attesting Officer*

NICHOLAS P. GODICI
*Acting Director of the United States Patent and Trademark Office*

SEQUENCE LISTING (1) GENERAL INFORMATION:

(iii) NUMBER OF SEQUENCES: 75

(2) INFORMATION FOR SEQ ID NO:1:

(i) SEQUENCE CHARACTERISTICS:
      (A) LENGTH: 2630 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 119..1645

(xi) SEQUENCE DESCRIPTION: SEQ ID NO:1:

```
ACCGTGCCTC TGCGGCCTGC GTGCCCGGAG TCCCCGCCTG TGTCGTCTCT GTCGCCGTCC        60

CCGTCTCCTG CCAGGCGCGG AGCCCTGCGA GCCGCGGGTG GGCCCCAGGC GCGCAGAC        118

ATG GGC TGC TCC GCC AAA GCG CGC TGG GCT GCC GGG GCG CTG GGC GTC        166
Met Gly Cys Ser Ala Lys Ala Arg Trp Ala Ala Gly Ala Leu Gly Val
  1               5                  10                  15

GCG GGG CTA CTG TGC GCT GTG CTG GGC GCT GTC ATG ATC GTG ATG GTG        214
Ala Gly Leu Leu Cys Ala Val Leu Gly Ala Val Met Ile Val Met Val
             20                  25                  30

CCG TCG CTC ATC AAG CAG CAG GTC CTT AAG AAC GTG CGC ATC GAC CCC        262
Pro Ser Leu Ile Lys Gln Gln Val Leu Lys Asn Val Arg Ile Asp Pro
         35                  40                  45

AGT AGC CTG TCC TTC AAC ATG TGG AAG GAG ATC CCT ATC CCC TTC TAT        310
Ser Ser Leu Ser Phe Asn Met Trp Lys Glu Ile Pro Ile Pro Phe Tyr
     50                  55                  60

CTC TCC GTC TAC TTC TTT GAC GTC ATG AAC CCC AGC GAG ATC CTG AAG        358
Leu Ser Val Tyr Phe Phe Asp Val Met Asn Pro Ser Glu Ile Leu Lys
 65                  70                  75                  80

GGC GAG AAG CCG CAG GTG CGG GAG CGC GGG CCC TAC GTG TAC AGG GAG        406
Gly Glu Lys Pro Gln Val Arg Glu Arg Gly Pro Tyr Val Tyr Arg Glu
                 85                  90                  95

TTC AGG CAC AAA AGC AAC ATC ACC TTC AAC AAC AAC GAC ACC GTG TCC        454
Phe Arg His Lys Ser Asn Ile Thr Phe Asn Asn Asn Asp Thr Val Ser
            100                 105                 110

TTC CTC GAG TAC CGC ACC TTC CAG TTC CAG CCC TCC AAG TCC CAC GGC        502
Phe Leu Glu Tyr Arg Thr Phe Gln Phe Gln Pro Ser Lys Ser His Gly
        115                 120                 125

TCG GAG AGC GAC TAC ATC GTC ATG CCC AAC ATC CTG GTC TTG GGT GCG        550
Ser Glu Ser Asp Tyr Ile Val Met Pro Asn Ile Leu Val Leu Gly Ala
    130                 135                 140

GCG GTG ATG ATG GAG AAT AAG CCC ATG ACC CTG AAG CTC ATC ATG ACC        598
Ala Val Met Met Glu Asn Lys Pro Met Thr Leu Lys Leu Ile Met Thr
145                 150                 155                 160
```

| | | | | | | | | | | | | | |
|---|---|---|---|---|---|---|---|---|---|---|---|---|---|
| TTG | GCA | TTC | ACC | ACC | CTC | GGC | GAA | CGT | GCC | TTC | ATG | AAC | CGC | ACT | GTG | 646 |
| Leu | Ala | Phe | Thr | Thr | Leu | Gly | Glu | Arg | Ala | Phe | Met | Asn | Arg | Thr | Val |
| | | | | 165 | | | | | 170 | | | | | 175 |

```
TTG GCA TTC ACC ACC CTC GGC GAA CGT GCC TTC ATG AAC CGC ACT GTG        646
Leu Ala Phe Thr Thr Leu Gly Glu Arg Ala Phe Met Asn Arg Thr Val
            165                 170                 175

GGT GAG ATC ATG TGG GGC TAC AAG GAC CCC CTT GTG AAT CTC ATC AAC        694
Gly Glu Ile Met Trp Gly Tyr Lys Asp Pro Leu Val Asn Leu Ile Asn
            180                 185                 190

AAG TAC TTT CCA GGC ATG TTC CCC TTC AAG GAC AAG TTC GGA TTA TTT        742
Lys Tyr Phe Pro Gly Met Phe Pro Phe Lys Asp Lys Phe Gly Leu Phe
            195                 200                 205

GCT GAG CTC AAC AAC TCC GAC TCT GGG CTC TTC ACG GTG TTC ACG GGG        790
Ala Glu Leu Asn Asn Ser Asp Ser Gly Leu Phe Thr Val Phe Thr Gly
            210                 215                 220

GTC CAG AAC ATC AGC AGG ATC CAC CTC GTG GAC AAG TGG AAC GGG CTG        838
Val Gln Asn Ile Ser Arg Ile His Leu Val Asp Lys Trp Asn Gly Leu
225             230                 235                 240

AGC AAG GTT GAC TTC TGG CAT TCC GAT CAG TGC AAC ATG ATC AAT GGA        886
Ser Lys Val Asp Phe Trp His Ser Asp Gln Cys Asn Met Ile Asn Gly
            245                 250                 255

ACT TCT GGG CAA ATG TGG CCG CCC TTC ATG ACT CCT GAG TCC TCG CTG        934
Thr Ser Gly Gln Met Trp Pro Pro Phe Met Thr Pro Glu Ser Ser Leu
            260                 265                 270

GAG TTC TAC AGC CCG GAG GCC TGC CGA TCC ATG AAG CTA ATG TAC AAG        982
Glu Phe Tyr Ser Pro Glu Ala Cys Arg Ser Met Lys Leu Met Tyr Lys
            275                 280                 285

GAG TCA GGG GTG TTT GAA GGC ATC CCC ACC TAT CGC TTC GTG GCT CCC       1030
Glu Ser Gly Val Phe Glu Gly Ile Pro Thr Tyr Arg Phe Val Ala Pro
290             295                 300

AAA ACC CTG TTT GCC AAC GGG TCC ATC TAC CCA CCC AAC GAA GGC TTC       1078
Lys Thr Leu Phe Ala Asn Gly Ser Ile Tyr Pro Pro Asn Glu Gly Phe
305             310                 315                 320

TGC CCG TGC CTG GAG TCT GGA ATT CAG AAC GTC AGC ACC TGC AGG TTC       1126
Cys Pro Cys Leu Glu Ser Gly Ile Gln Asn Val Ser Thr Cys Arg Phe
            325                 330                 335

AGT GCC CCC TTG TTT CTC TCC CAT CCT CAC TTC CTC AAC GCC GAC CCG       1174
Ser Ala Pro Leu Phe Leu Ser His Pro His Phe Leu Asn Ala Asp Pro
            340                 345                 350

GTT CTG GCA GAA GCG GTG ACT GGC CTG CAC CCT AAC CAG GAG GCA CAC       1222
Val Leu Ala Glu Ala Val Thr Gly Leu His Pro Asn Gln Glu Ala His
            355                 360                 365

TCC TTG TTC CTG GAC ATC CAC CCG GTC ACG GGA ATC CCC ATG AAC TGC       1270
Ser Leu Phe Leu Asp Ile His Pro Val Thr Gly Ile Pro Met Asn Cys
370             375                 380

TCT GTG AAA CTG CAG CTG AGC CTC TAC ATG AAA TCT GTC GCA GGC ATT       1318
Ser Val Lys Leu Gln Leu Ser Leu Tyr Met Lys Ser Val Ala Gly Ile
385             390                 395                 400

GGA CAA ACT GGG AAG ATT GAG CCT GTG GTC CTG CCG CTG CTC TGG TTT       1366
Gly Gln Thr Gly Lys Ile Glu Pro Val Val Leu Pro Leu Leu Trp Phe
            405                 410                 415

GCA GAG AGC GGG GCC ATG GAG GGG GAG ACT CTT CAC ACA TTC TAC ACT       1414
Ala Glu Ser Gly Ala Met Glu Gly Glu Thr Leu His Thr Phe Tyr Thr
            420                 425                 430

CAG CTG GTG TTG ATG CCC AAG GTG ATG CAT TAT GCC CAG TAC GTC CTC       1462
Gln Leu Val Leu Met Pro Lys Val Met His Tyr Ala Gln Tyr Val Leu
            435                 440                 445

CTG GCG CTG GGC TGC GTC CTG CTG CTG GTC CCT GTC ATC TGC CAA ATC       1510
Leu Ala Leu Gly Cys Val Leu Leu Leu Val Pro Val Ile Cys Gln Ile
450             455                 460

CGG AGC CAA GAG AAA TGC TAT TTA TTT TGG AGT AGT AGT AAA AAG GGC       1558
Arg Ser Gln Glu Lys Cys Tyr Leu Phe Trp Ser Ser Ser Lys Lys Gly
465             470                 475                 480
```

```
TCA AAG GAT AAG GAG GCC ATT CAG GCC TAT TCT GAA TCC CTG ATG ACA    1606
Ser Lys Asp Lys Glu Ala Ile Gln Ala Tyr Ser Glu Ser Leu Met Thr
            485                 490                 495

TCA GCT CCC AAG GGC TCT GTG CTG CAG GAA GCA AAA CTG TAGGGTCCTG    1655
Ser Ala Pro Lys Gly Ser Val Leu Gln Glu Ala Lys Leu
            500                 505

AGGACACCGT GAGCCAGCCA GGCCTGGCCG CTGGGCCTGA CCGGCCCCCC AGCCCCTACA    1715

CCCCGCTTCT CCCGGACTCT CCCAGCAGAC AGCCCCCCAG CCCCACAGCC TGAGCCTCCC    1775

AGCTGCCATG TGCCTGTTGC ACACCTGCAC ACACGCCCTG GCACACATAC ACACATGCGT    1835

GCAGGCTTGT GCAGACACTC AGGGATGGAG CTGCTGCTGA AGGGACTTGT AGGGAGAGGC    1895

TCGTCAACAA GCACTGTTCT GGAACCTTCT CTCCACGTGG CCCACAGGCC TGACCACAGG    1955

GGCTGTGGGT CCTGCGTCCC CTTCCTCGGG TGAGCCTGGC CTGTCCCGTT CAGCCGTTGG    2015

GCCCAGGCTT CCTCCCCTCC AAGGTGAAAC ACTGCAGTCC CGGTGTGGTG GCTCCCCATG    2075

CAGGACGGGC CAGGCTGGGA GTGCCGCCTT CCTGTGCCAA ATTCAGTGGG GACTCAGTGC    2135

CCAGGCCCTG GCCACGAGCT TTGGCCTTGG TCTACCTGCC AGGCCAGGCA AAGCGCCTTT    2195

ACACAGGCCT CGGAAAACAA TGGAGTGAGC ACAAGATGCC CTGTGCAGCT GCCCGAGGGT    2255

CTCCGCCCAC CCCGGCCGGA CTTTGATCCC CCGAAGTCT TCACAGGCAC TGCATCGGGT    2315

TGTCTGGCGC CCTTTTCCTC CAGCCTAAAC TGACATCATC CTATGGACTG AGCCGGCCAC    2375

TYTYTGGCCG AAGTGGCCGC AGGCTGTGCC CCCGAGCTGC CCCCACCCCC TCACAGGGTC    2435

CCTCAGATTA TAGGTGCCCA GGCTGAGGTG AAGAGGCCTG GGGGCCCTGC CTTCCGGGCG    2495

CTCCTGGACC CTGGGGCAAA CCTGTGACCC TTTTCTACTG GAATAGAAAT GAGTTTTATC    2555

ATCTTTGAAA AATAATTCAC TCTTGAAGTA ATAAACGTTT AAAAAAATGG GAAAAAAAA    2615

AAAAAAAAAA AAAAA    2630

(2) INFORMATION FOR SEQ ID NO:2:

(i) SEQUENCE CHARACTERISTICS:
        (A) LENGTH: 509 amino acids
        (B) TYPE: amino acid
        (D) TOPOLOGY: linear (ii) MOLECULE TYPE: protein (xi) SEQUENCE DESCRIPTION: SEQ ID NO:2:

Met Gly Cys Ser Ala Lys Ala Arg Trp Ala Gly Ala Leu Gly Val
 1               5                   10                  15

Ala Gly Leu Leu Cys Ala Val Leu Gly Ala Val Met Ile Val Met Val
                20                  25                  30

Pro Ser Leu Ile Lys Gln Gln Val Leu Lys Asn Val Arg Ile Asp Pro
            35                  40                  45

Ser Ser Leu Ser Phe Asn Met Trp Lys Glu Ile Pro Ile Pro Phe Tyr
        50                  55                  60

Leu Ser Val Tyr Phe Phe Asp Val Met Asn Pro Ser Glu Ile Leu Lys
 65                 70                  75                  80

Gly Glu Lys Pro Gln Val Arg Glu Arg Gly Pro Tyr Val Tyr Arg Glu
                85                  90                  95

Phe Arg His Lys Ser Asn Ile Thr Phe Asn Asn Asn Asp Thr Val Ser
            100                 105                 110

Phe Leu Glu Tyr Arg Thr Phe Gln Phe Gln Pro Ser Lys Ser His Gly
        115                 120                 125

Ser Glu Ser Asp Tyr Ile Val Met Pro Asn Ile Leu Val Leu Gly Ala
```

```
                130                 135                 140
Ala Val Met Met Glu Asn Lys Pro Met Thr Leu Lys Leu Ile Met Thr
145                 150                 155                 160

Leu Ala Phe Thr Thr Leu Gly Glu Arg Ala Phe Met Asn Arg Thr Val
                165                 170                 175

Gly Glu Ile Met Trp Gly Tyr Lys Asp Pro Leu Val Asn Leu Ile Asn
                180                 185                 190

Lys Tyr Phe Pro Gly Met Phe Pro Phe Lys Asp Lys Phe Gly Leu Phe
                195                 200                 205

Ala Glu Leu Asn Asn Ser Asp Ser Gly Leu Phe Thr Val Phe Thr Gly
210                 215                 220

Val Gln Asn Ile Ser Arg Ile His Leu Val Asp Lys Trp Asn Gly Leu
225                 230                 235                 240

Ser Lys Val Asp Phe Trp His Ser Asp Gln Cys Asn Met Ile Asn Gly
                245                 250                 255

Thr Ser Gly Gln Met Trp Pro Pro Phe Met Thr Pro Glu Ser Ser Leu
                260                 265                 270

Glu Phe Tyr Ser Pro Glu Ala Cys Arg Ser Met Lys Leu Met Tyr Lys
                275                 280                 285

Glu Ser Gly Val Phe Glu Gly Ile Pro Thr Tyr Arg Phe Val Ala Pro
290                 295                 300

Lys Thr Leu Phe Ala Asn Gly Ser Ile Tyr Pro Pro Asn Glu Gly Phe
305                 310                 315                 320

Cys Pro Cys Leu Glu Ser Gly Ile Gln Asn Val Ser Thr Cys Arg Phe
                325                 330                 335

Ser Ala Pro Leu Phe Leu Ser His Pro His Phe Leu Asn Ala Asp Pro
                340                 345                 350

Val Leu Ala Glu Ala Val Thr Gly Leu His Pro Asn Gln Glu Ala His
                355                 360                 365

Ser Leu Phe Leu Asp Ile His Pro Val Thr Gly Ile Pro Met Asn Cys
370                 375                 380

Ser Val Lys Leu Gln Leu Ser Leu Tyr Met Lys Ser Val Ala Gly Ile
385                 390                 395                 400

Gly Gln Thr Gly Lys Ile Glu Pro Val Val Leu Pro Leu Leu Trp Phe
                405                 410                 415

Ala Glu Ser Gly Ala Met Glu Gly Glu Thr Leu His Thr Phe Tyr Thr
                420                 425                 430

Gln Leu Val Leu Met Pro Lys Val Met His Tyr Ala Gln Tyr Val Leu
                435                 440                 445

Leu Ala Leu Gly Cys Val Leu Leu Val Pro Val Ile Cys Gln Ile
450                 455                 460

Arg Ser Gln Glu Lys Cys Tyr Leu Phe Trp Ser Ser Lys Lys Gly
465                 470                 475                 480

Ser Lys Asp Lys Glu Ala Ile Gln Ala Tyr Ser Glu Ser Leu Met Thr
                485                 490                 495

Ser Ala Pro Lys Gly Ser Val Leu Gln Glu Ala Lys Leu
                500                 505

(2) INFORMATION FOR SEQ ID NO:3:

(i) SEQUENCE CHARACTERISTICS:
        (A) LENGTH: 1825 base pairs
        (B) TYPE: nucleic acid
        (C) STRANDEDNESS: single
        (D) TOPOLOGY: linear
```

(ii) MOLECULE TYPE: cDNA (ix) FEATURE:
    (A) NAME/KEY: CDS
    (B) LOCATION: 156..1682

(xi) SEQUENCE DESCRIPTION: SEQ ID NO:3:

```
GCCACCTGCA GGGCTACTGC TGCTCCGGCC ACTGCCTGAG ACTCACCTTG CTGGAACGTG      60

AGCCTCGGCT TCTGTCATCT CTGTGGCCTC TGTCGCTTCT GTCGCTGTCC CCCTTCAGTC     120

CCTGAGCCCC GCGAGCCCGG GCCGCACACG CGGAC ATG GGC GGC AGC GCC AGG        173
                                      Met Gly Gly Ser Ala Arg
                                        1               5

GCG CGC TGG GTG GCG GTG GGG CTG GGC GTC GTG GGG CTG CTG TGC GCT       221
Ala Arg Trp Val Ala Val Gly Leu Gly Val Val Gly Leu Leu Cys Ala
             10                  15                  20

GTG CTC GGT GTG GTT ATG ATC CTC GTG ATG CCC TCG CTC ATC AAA CAG       269
Val Leu Gly Val Val Met Ile Leu Val Met Pro Ser Leu Ile Lys Gln
         25                  30                  35

CAG GTA CTG AAG AAT GTC CGC ATA GAC CCC AGC AGC CTG TCC TTT GCA       317
Gln Val Leu Lys Asn Val Arg Ile Asp Pro Ser Ser Leu Ser Phe Ala
     40                  45                  50

ATG TGG AAG GAG ATC CCT GTA CCC TTC TAC TTG TCC GTC TAC TTC TTC       365
Met Trp Lys Glu Ile Pro Val Pro Phe Tyr Leu Ser Val Tyr Phe Phe
 55                  60                  65                  70

GAG GTG GTC AAT CCC AGC GAG ATC CTA AAG GGT GAG AAG CCA GTA GTG       413
Glu Val Val Asn Pro Ser Glu Ile Leu Lys Gly Glu Lys Pro Val Val
                 75                  80                  85

CGG GAG CGT GGA CCC TAT GTC TAC AGG GAA TTC AGA CAT AAG GCC AAC       461
Arg Glu Arg Gly Pro Tyr Val Tyr Arg Glu Phe Arg His Lys Ala Asn
             90                  95                 100

ATC ACC TTC AAT GAC AAT GAT ACT GTG TCC TTT GTG GAG CAC CGC AGC       509
Ile Thr Phe Asn Asp Asn Asp Thr Val Ser Phe Val Glu His Arg Ser
        105                 110                 115

CTC CAT TTC CAG CCG GAC AGG TCC CAC GGC TCT GAG AGT GAC TAC ATT       557
Leu His Phe Gln Pro Asp Arg Ser His Gly Ser Glu Ser Asp Tyr Ile
    120                 125                 130

ATA CTG CCT AAC ATT CTG GTC TTG GGG GGC GCA GTA ATG ATG GAG AGC       605
Ile Leu Pro Asn Ile Leu Val Leu Gly Gly Ala Val Met Met Glu Ser
135                 140                 145                 150

AAG TCT GCA GGC CTG AAG CTG ATG ATG ACC TTG GGG CTG GCC ACC TTG       653
Lys Ser Ala Gly Leu Lys Leu Met Met Thr Leu Gly Leu Ala Thr Leu
                155                 160                 165

GGC CAG CGT GCC TTT ATG AAC CGA ACA GTT GGT GAG ATC CTG TGG GGC       701
Gly Gln Arg Ala Phe Met Asn Arg Thr Val Gly Glu Ile Leu Trp Gly
            170                 175                 180

TAT GAG GAT CCC TTC GTG AAT TTT ATC AAC AAA TAC TTA CCA GAC ATG       749
Tyr Glu Asp Pro Phe Val Asn Phe Ile Asn Lys Tyr Leu Pro Asp Met
        185                 190                 195

TTC CCC ATC AAG GGC AAG TTC GGC CTG TTT GTT GAG ATG AAC AAC TCA       797
Phe Pro Ile Lys Gly Lys Phe Gly Leu Phe Val Glu Met Asn Asn Ser
    200                 205                 210

GAC TCT GGG CTC TTC ACT GTG TTC ACG GGC GTC CAG AAC TTC AGC AAG       845
Asp Ser Gly Leu Phe Thr Val Phe Thr Gly Val Gln Asn Phe Ser Lys
215                 220                 225                 230

ATC CAC CTG GTG GAC AGA TGG AAT GGG CTC AGC AAG GTC AAC TAC TGG       893
Ile His Leu Val Asp Arg Trp Asn Gly Leu Ser Lys Val Asn Tyr Trp
                235                 240                 245

CAT TCA GAG CAG TGC AAC ATG ATC AAT GGC ACT TCC GGG CAG ATG TGG       941
His Ser Glu Gln Cys Asn Met Ile Asn Gly Thr Ser Gly Gln Met Trp
            250                 255                 260
```

```
GCA CCA TTC ATG ACA CCC CAG TCC TCG CTG GAA TTC TTC AGT CCG GAA          989
Ala Pro Phe Met Thr Pro Gln Ser Ser Leu Glu Phe Phe Ser Pro Glu
            265                 270                 275

GCC TGC AGG TCT ATG AAG CTC ACC TAC CAT GAT TCA GGG GTG TTT GAA         1037
Ala Cys Arg Ser Met Lys Leu Thr Tyr His Asp Ser Gly Val Phe Glu
    280                 285                 290

GGC ATC CCC ACC TAT CGC TTC ACA GCC CCT AAA ACT TTG TTT GCC AAT         1085
Gly Ile Pro Thr Tyr Arg Phe Thr Ala Pro Lys Thr Leu Phe Ala Asn
295                 300                 305                 310

GGG TCT GTT TAC CCA CCC AAT GAA GGT TTC TGC CCG TGC CTT GAA TCC         1133
Gly Ser Val Tyr Pro Pro Asn Glu Gly Phe Cys Pro Cys Leu Glu Ser
                315                 320                 325

GGC ATT CAA AAT GTC AGC ACT TGC AGG TTT GGT GCA CCC CTG TTT CTG         1181
Gly Ile Gln Asn Val Ser Thr Cys Arg Phe Gly Ala Pro Leu Phe Leu
            330                 335                 340

TCA CAC CCT CAC TTC TAC AAT GCA GAC CCT GTG CTA TCA GAA GCC GTT         1229
Ser His Pro His Phe Tyr Asn Ala Asp Pro Val Leu Ser Glu Ala Val
            345                 350                 355

CTG GGT CTG AAC CCT GAC CCA AGG GAG CAT TCT TTG TTC CTT GAC ATC         1277
Leu Gly Leu Asn Pro Asp Pro Arg Glu His Ser Leu Phe Leu Asp Ile
360                 365                 370

CAT CCG GTC ACT GGG ATC CCC ATG AAC TGT TCT GTG AAG TTG CAG ATA         1325
His Pro Val Thr Gly Ile Pro Met Asn Cys Ser Val Lys Leu Gln Ile
375                 380                 385                 390

AGC CTC TAC ATC AAA GCT GTC AAG GGC ATT GGG CAA ACA GGG AAG ATC         1373
Ser Leu Tyr Ile Lys Ala Val Lys Gly Ile Gly Gln Thr Gly Lys Ile
                395                 400                 405

GAG CCC GTG GTC CTC CCA TTG CTG TGG TTT GAG CAG AGC GGT GCC ATG         1421
Glu Pro Val Val Leu Pro Leu Leu Trp Phe Glu Gln Ser Gly Ala Met
            410                 415                 420

GGC GGC GAG CCC CTG AAC ACG TTC TAC ACG CAG CTG GTG CTG ATG CCC         1469
Gly Gly Glu Pro Leu Asn Thr Phe Tyr Thr Gln Leu Val Leu Met Pro
            425                 430                 435

CAG GTA CTT CAG TAT GTG CAG TAT GTG CTG CTG GGG CTG GGC GGC CTC         1517
Gln Val Leu Gln Tyr Val Gln Tyr Val Leu Leu Gly Leu Gly Gly Leu
440                 445                 450

CTG CTG CTG GTG CCC GTC ATC TAC CAG TTG CGC AGC CAG GAG AAA TGC         1565
Leu Leu Leu Val Pro Val Ile Tyr Gln Leu Arg Ser Gln Glu Lys Cys
455                 460                 465                 470

TTT TTA TTT TGG AGT GGT AGT AAA AAG GGC TCG CAG GAT AAG GAG GCC         1613
Phe Leu Phe Trp Ser Gly Ser Lys Lys Gly Ser Gln Asp Lys Glu Ala
                475                 480                 485

ATT CAG GCC TAC TCT GAG TCT CTG ATG TCA CCA GCT GCC AAG GGC ACG         1661
Ile Gln Ala Tyr Ser Glu Ser Leu Met Ser Pro Ala Ala Lys Gly Thr
            490                 495                 500

GTG CTG CAA GAA GCC AAG CTG TAGGGTCCCA AAGACACCAC GAGCCCCCCC           1712
Val Leu Gln Glu Ala Lys Leu
                505

AACCTGATAG CTTGGTCAGA CCAGCCATCC AGCCCCTACA CCCCGCTTCT TGAGGACTCT       1772

CTCAGCGGAC AGTCCGCCAG TGCCATGGCC TGAGCCCCAG ATGTCACACC TGT              1825

(2) INFORMATION FOR SEQ ID NO:4:

(i) SEQUENCE CHARACTERISTICS:
        (A) LENGTH: 509 amino acids
        (B) TYPE: amino acid
        (D) TOPOLOGY: linear (ii) MOLECULE TYPE: protein (xi) SEQUENCE DESCRIPTION: SEQ ID NO:4:
```

```
Met Gly Gly Ser Ala Arg Ala Arg Trp Val Ala Val Gly Leu Gly Val
 1               5                  10                 15

Val Gly Leu Leu Cys Ala Val Leu Gly Val Met Ile Leu Val Met
         20                  25                  30

Pro Ser Leu Ile Lys Gln Gln Val Leu Lys Asn Val Arg Ile Asp Pro
             35                  40                  45

Ser Ser Leu Ser Phe Ala Met Trp Lys Glu Ile Pro Val Pro Phe Tyr
 50                  55                  60

Leu Ser Val Tyr Phe Phe Glu Val Val Asn Pro Ser Glu Ile Leu Lys
 65                  70                  75                  80

Gly Glu Lys Pro Val Val Arg Glu Arg Gly Pro Tyr Val Tyr Arg Glu
                 85                  90                  95

Phe Arg His Lys Ala Asn Ile Thr Phe Asn Asp Asn Asp Thr Val Ser
             100                 105                 110

Phe Val Glu His Arg Ser Leu His Phe Gln Pro Asp Arg Ser His Gly
             115                 120                 125

Ser Glu Ser Asp Tyr Ile Ile Leu Pro Asn Ile Leu Val Leu Gly Gly
 130                 135                 140

Ala Val Met Met Glu Ser Lys Ser Ala Gly Leu Lys Leu Met Met Thr
145                 150                 155                 160

Leu Gly Leu Ala Thr Leu Gly Gln Arg Ala Phe Met Asn Arg Thr Val
                 165                 170                 175

Gly Glu Ile Leu Trp Gly Tyr Glu Asp Pro Phe Val Asn Phe Ile Asn
                 180                 185                 190

Lys Tyr Leu Pro Asp Met Phe Pro Ile Lys Gly Lys Phe Gly Leu Phe
             195                 200                 205

Val Glu Met Asn Asn Ser Asp Ser Gly Leu Phe Thr Val Phe Thr Gly
 210                 215                 220

Val Gln Asn Phe Ser Lys Ile His Leu Val Asp Arg Trp Asn Gly Leu
225                 230                 235                 240

Ser Lys Val Asn Tyr Trp His Ser Glu Gln Cys Asn Met Ile Asn Gly
                 245                 250                 255

Thr Ser Gly Gln Met Trp Ala Pro Phe Met Thr Pro Gln Ser Ser Leu
                 260                 265                 270

Glu Phe Phe Ser Pro Glu Ala Cys Arg Ser Met Lys Leu Thr Tyr His
             275                 280                 285

Asp Ser Gly Val Phe Glu Gly Ile Pro Thr Tyr Arg Phe Thr Ala Pro
 290                 295                 300

Lys Thr Leu Phe Ala Asn Gly Ser Val Tyr Pro Pro Asn Glu Gly Phe
305                 310                 315                 320

Cys Pro Cys Leu Glu Ser Gly Ile Gln Asn Val Ser Thr Cys Arg Phe
                 325                 330                 335

Gly Ala Pro Leu Phe Leu Ser His Pro His Phe Tyr Asn Ala Asp Pro
                 340                 345                 350

Val Leu Ser Glu Ala Val Leu Gly Leu Asn Pro Asp Pro Arg Glu His
             355                 360                 365

Ser Leu Phe Leu Asp Ile His Pro Val Thr Gly Ile Pro Met Asn Cys
 370                 375                 380

Ser Val Lys Leu Gln Ile Ser Leu Tyr Ile Lys Ala Val Lys Gly Ile
385                 390                 395                 400

Gly Gln Thr Gly Lys Ile Glu Pro Val Leu Pro Leu Leu Trp Phe
                 405                 410                 415

Glu Gln Ser Gly Ala Met Gly Gly Glu Pro Leu Asn Thr Phe Tyr Thr
             420                 425                 430
```

```
Gln Leu Val Leu Met Pro Gln Val Leu Gln Tyr Val Gln Tyr Val Leu
            435                 440                 445

Leu Gly Leu Gly Gly Leu Leu Leu Val Pro Val Ile Tyr Gln Leu
        450                 455                 460

Arg Ser Gln Glu Lys Cys Phe Leu Phe Trp Ser Gly Ser Lys Lys Gly
465                 470                 475                 480

Ser Gln Asp Lys Glu Ala Ile Gln Ala Tyr Ser Glu Ser Leu Met Ser
                485                 490                 495

Pro Ala Ala Lys Gly Thr Val Leu Gln Glu Ala Lys Leu
                500                 505

(2) INFORMATION FOR SEQ ID NO:5:

(i) SEQUENCE CHARACTERISTICS:
        (A) LENGTH: 1002 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

ACTGCGGAGA TGAGGGTCTA GAAGGTGGTG GCGGGGCATG TGGACCGTTG TAAGGGCTCT          60

GGGGTTCCTG GGTGGGCTGG CGAAGTCCTA CTCACAGTGA CCAACCATGA TGATGGTCCC        120

GATAGAGGAG GAGAGGGAGG AGGAGGGAAA AGGAAGGGTG AGGGGCTCAG AGGGGAGAGC        180

TGGGAGGAGG GGAGACATAG GTGGGGGAAG GGGTAGGAGA AAGGGGAAGG GAGCAAGAGG        240

GTGAGGGGCA CCAGGCCCCA TAGACGTTTT GGCTCAGCGG CCACGAGGCT TCATCAGCTC        300

CCGCCCCAAA ACGGAAGCGA GGCCGTGGGG GCAGCGGCAG CATGGCGGGG CTTGTCTTGG        360

CGGCCATGGC CCCGCCCCCT GCCCGTCCGA TCAGCGCCCC GCCCCGTCCC CGCCCCGACC        420

CCGCCCCGGG CCCGCTCAGG CCCCGCCCCT GCCGCCGGAA TCCTGAAGCC CAAGGCTGCC        480

CGGGGGCGGT CCGGCGGCGC CGGCGATGGG GCATAAAACC ACTGGCCACC TGCCGGGCTG        540

CTCCTGCGTG CGCTGCCGTC CCGGATCCAC CGTGCCTCTG CGGCCTGCGT GCCCCGAGTC        600

CCCGCCTGTG TCGTCTCTGT CGCCGTCCCC GTCTCCTGCC AGGCGCGGAG CCCTGCGAGC        660

CGCGGGTGGG CCCCAGGCGC GCAGACATGG GCTGCTCCGC CAAAGCGCGC TGGGCTGCCG        720

GGGCGCTGGG CGTCGCGGGG CTACTGTGCG CTGTGCTGGG CGCTGTCATG ATCGTGATGG        780

TGCCGTCGCT CATCAAGCAG CAGGTCCTTA AGGTGGGTGA GGGAGACCCC AGGGGGTCCG        840

CGCACGGACC CGGGCTGTTG GGCGCTGGGC GCCGGGAGGA CCCGCGCGTT GCGGTGGGTG        900

GGCGACCGCA GCGGAATCGG CGCCCGGGCC TGGCGCCGCA GAACACGAGG GAGGCCAGGC        960

GCTTCGGGAG GGGCTGCTGC CCGCCTCCCC ACCACCCTCA CC                         1002

(2) INFORMATION FOR SEQ ID NO:6:

(i) SEQUENCE CHARACTERISTICS:
        (A) LENGTH: 479 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

AGCCTCATGT GCGAAGGGCT TTCCCACCAC CTCCTATCCC AAGCTCCCGC CGAGGAGCCC         60

CTTCCCTGGC CGGGCTCGGG CAGCTGTTCC GGAGCCTTGT GGTGGGGCGT GGGGCCCTCA        120
```

-continued

```
TCACTCTCCT CACAAGCGTA CTTGTCCCTT CCCCTGCAGA ACGTGCGCAT CGACCCCAGT    180

AGCCTGTCCT TCAACATGTG GAAGGAGATC CCTATCCCCT TCTATCTCTC CGTCTACTTC    240

TTTGACGTCA TGAACCCCAG CGAGATCCTG AAGGGCGAGA AGCCGCAGGT GCGGGAGCGC    300

GGGCCCTACG TGTACAGGTG AGGCTGTGTC CACGTGATGG TGGACGGGCC GGCTGACGCT    360

GGGCATGGGA CGGGTCTCAA GTGGACGGGA TGGGGAGGCT GCTGACTGAC CCCCAAACAT    420

TGTTCCGGAA GCACGCAACT CATAGTCGGG GTAAGTGCTA CTCCCAAAAA AGTTTGCGT    479
```

(2) INFORMATION FOR SEQ ID NO:7:

(i) SEQUENCE CHARACTERISTICS:
        (A) LENGTH: 495 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
CATGTCCTGC AGTGGGCAGG CAGCGGGAGG GACAGACTTG GCGAAGGGGC CGAGCTCAGC     60

TTTGGCTGTG GGGCCGGAGG TGTGCACAGA CGTCCAGGGC CCCTGGTTCC CAGGCAGGCA    120

TTGCAGGCGA GTAGAAGGGA AACGTCCCAT GCAGCGGGGC GGGGCGTCTG ACCCACTGGC    180

TTCCCCCACA GGGAGTTCAG GCACAAAAGC AACATCACCT TCAACAACAA CGACACCGTG    240

TCCTTCCTCG AGTACCGCAC CTTCCAGTTC CAGCCCTCCA AGTCCACGG CTCGGAGAGC     300

GACTACATCG TCATGCCCAA CATCCTGGTC TTGGTGAGGC TGCCCTGTGG CCCACGCCGC    360

CTCGCACCCT GACCTCGTCC CCTGTCTCTC CTCCCGCCTG CCCCTTGTGC AGAGAGCAGT    420

CCCTGAGGTG GTCGGAGCGT GGGGACTCAC GCCTGGTGGG TGGCTTTCGG CCCTGTGCTG    480

TCTCCACCAC CCCCA                                                    495
```

(2) INFORMATION FOR SEQ ID NO:8:

(i) SEQUENCE CHARACTERISTICS:
        (A) LENGTH: 526 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
GGTGGTTCTG GTGTCCCAGA TGCCCCACGT GGCCACTCCA GGGGCCTCCT GCACCCCAGC     60

ATTTCCCTTC ATGGGCTCTT TGCTGTGAGG CCCAGCTGGG GCCAAGGGAG GATGGGCCAG    120

CCACGTCCAG CCTCTGACAC TAGTGTCCCT TCGCCTTGCA GGGTGCGGCG GTGATGATGG    180

AGAATAAGCC CATGACCCTG AAGCTCATCA TGACCTTGGC ATTCACCACC CTCGGCGAAC    240

GTGCCTTCAT GAACCGCACT GTGGGTGAGA TCATGTGGGG CTACAAGGAC CCCTTGTGAA    300

TCTCATCAAC AAGTACTTTC CAGGCATGTT CCCCTTCAAG GACAAGTTCG GATTATTTGC    360

TGAGGTACGT GTGGCCTGGT GAGAAGCCAA AGATTCAGGC CTGTGTCCTG TCTTCCCCTC    420

ACACAGCCTG GACACTGGTC ACCAGCTTGC TTTGTAGCTG GCTGGGGATC TAGTGGCTGT    480

GGGTTGTAAG TGACTGAGAA CCTGACTCAA ACCGGCTTGA GTGAAA                  526
```

(2) INFORMATION FOR SEQ ID NO:9:

(i) SEQUENCE CHARACTERISTICS:
        (A) LENGTH: 416 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:9:

CCTCTCGGTC CCCAGACACT GGGCATTTGG CAGTGAACCA GATGCTGGGG GCCCTGTCCT      60

TCTGGTGGAG GGGGAGGAGG GCTCAGCCCA GAATGTTCAG ACCAGGCCGG CTCAATGGCA     120

GGCCTAAGCC TTACGATGCT GTTCCCTGCT GTGTCTGTAG CTCAACAACT CCGACTCTGG     180

GCTCTTCACG GTGTTCACGG GGGTCCAGAA CATCAGCAGG ATCCACCTCG TGGACAAGTG     240

GAACGGGCTG AGCAAGGTGA GGGGCGAGAG GCGAGGGCCC CTGTCGCCAG GGAGAGGGGA     300

GGGTGGGCCC GGCCATGGCT GCTCGGGAGT GGCAGGGACC AGAGAGCTCC TTCTTCCTTT     360

GTCGTGAAGA GGGTGCTGGG AGGATGAACA CTCTTGAAGT TGGAGGAGGG ATTTTA         416

(2) INFORMATION FOR SEQ ID NO:10:

(i) SEQUENCE CHARACTERISTICS:
        (A) LENGTH: 436 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

TCTCTGTGTG TCTACATAGC CTGCCCTCTT CCCACCGTGC CAGTATTGGG AATTGAGTGG      60

CCGTGCGTGC ACCAGGGTGA GTTAGGTGTG CAGCACCTGA GAGGGCTTAT TAAGGGGCCT     120

TGGCCCTACT GAGGGGTCTA GTCTGGATGC TTCCCCCCAG GTTGACTTCT GGCATTCCGA     180

TCAGTGCAAC ATGATCAATG GAACTTCTGG GCAAATGTGG CCGCCCTTCA TGACTCCTGA     240

GTCCTCGCTG GAGTTCTACA GCCCGGAGGC CTGCCGGTAA TCACTGGGAC TCGGGGCCTC     300

CTGGGTTTCC TGGGTAGCTC ATGGCCAAAT TCTGTGGTGT TGGCTGTGCA CTTGGAAAGC     360

ATTTTGACTC ATCGTGGATT TGACTCAGTA GCCCTTGGCA CCAGCTTGAA TTCTCTTTGG     420

TCACACCACC AAAAGC                                                     436

(2) INFORMATION FOR SEQ ID NO:11:

(i) SEQUENCE CHARACTERISTICS:
        (A) LENGTH: 481 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GGAGGTCGCT GCAGCTCCGC GGGTGAGAGA TGGGGGCGGT TTGGACCCGG GAGGTGGTAG      60

CGCCCGTGGG GAGAAGTGGC TGGATCTGGG CAGCCTTTGG CAGGGCCTGG CTCTGGCCGC     120

CGGGTCTGGG TGTCCCCTCT CATCCTGTCT GTCCCCTGCA GATCCATGAA GCTAATGTAC     180

AAGGAGTCAG GGTGTTTGA AGGCATCCCC ACCTATCGCT TCGTGGCTCC CAAAACCCTG     240

TTTGCCAACG GTCCATCTA CCCACCCAAC GAAGGCTTCT GCCCGTGCCT GGAGTCTGGA     300

ATTCAGAACG TCAGCAGCTG CAGGTTCAGT ACGTGCCGTC CCTGTTCTG GGATNGCCGG     360

AGGGTGTTAG GTNTGGGCA CCTNANGGTT TATCTGCCCA ATGCTGTCTG CTTAATCTCT     420

GGCCTCTGTA CTCTTGATAA CCCATTAAGC CAAAAATATG ATGCCTCTGG GACGATATCT     480

G                                                                    481
```

(2) INFORMATION FOR SEQ ID NO:12:

(i) SEQUENCE CHARACTERISTICS:
        (A) LENGTH: 430 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
TGGGGCTTTT TACAGAATGG AGGAAGGGAT CCTCTCTGTC GGGTATTATG GTCATCGCCA      60
CGGGGGTGCC GTGCAGACCA CAGCTCTGTG CAGACTTCCG GAGTGGCAGG ACGTGCCAAT     120
ATACTGTCGT TGTATGATGT CCCCTCCCTG CCCTTGTTGT AGGTGCCCCC TTGTTTCTCT     180
CCCATCCTCA CTTCATCAAC GCCGACCCGG TTCTGGCAGA AGCGGTGACT GGCCTGCACC     240
CTAACCAGGA GGCACACTCC TTGTTCGTGG ACATCCACCC GGTGAGCCCC TGCCATCCTC     300
TGTGGGGGT GGGTGATTCC TGGTTGGAGC ACACCTGGCT GCCTCCTCTC TCCCCAGGCA     360
GAGAGCTGCT GTGGGCTGGG GTGGTGGGAA GCCTGGCTTC TAGAATCTCG AGCCACCAAA     420
GTTCCTTACT                                                            430
```

(2) INFORMATION FOR SEQ ID NO:13:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
CCCCAGCCTG TGGCTTGTTT TAGGTAAGAT ACAAGCAAGC TCCACTGGGC AGTTAGCTGG      60
GACGCCCACC CTCTTGACTG GGACCAGGGA AAAGAAGGTT GACTGTGTCC CTGGAGCTTG     120
GGGGTGGCCA GTCTCCTCAC TGTGTTTGTT GCCGCAGGTC ACGGGAATCC CCATGAACTG     180
CTCTGTGAAA CTGCAGCTGA GCCTCTACAT GAAATCTGTC GCAGGCATTG GGTGAGTGGG     240
GACTGGGAAC TGGGGCTGCA TTGCTCATTG AGAGATTANG TGCTCAGTGC TCCAGTGTTC     300
CCAGACTCCC CTGACATACC CCAGGAAACA GGGCATGGGG AAGGGAGAGG GTCCTATTGG     360
GGGTGGAATC CAGTCCCTGC TGATCTTCTC                                      390
```

(2) INFORMATION FOR SEQ ID NO:14:

(i) SEQUENCE CHARACTERISTICS:
        (A) LENGTH: 370 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
ATGGCTCCTA AAGTGTTTCA GCTCATTGTT TATATTTGGT GGTGAGGGTT TAGTGTGTGC      60
AAAATTATAC TAAACCTGTT TAGATGTTGT ATTCAAGCAG AATTAGATCA AGTTTGGGTG     120
TAAGACTTTG TTCCAACACC TATGTCTTGC TTATTTCCAG ACAAACTGGG AAGATTGAGC     180
CTGTGGTCCT GCCGCTGCTC TGGTTTGCAG AGGTAAGGGT GCGTTGGGCA CAGCGTCGGG     240
GGCTTTTGTT AATAGCCAAT GTGGGCATTT GAGGCAGGAG GCGGGGGGAG CACCTTGTAG     300
```

```
AAAGGGAGAG GGCTGAGCCA GGGTAACCGG ACTGTTACAT GGACCAGCGT ATCATACACT      360

TCACCCTGTC                                                            370

(2) INFORMATION FOR SEQ ID NO:15:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CCTGGAGGGA GGAGGTCCCT GGCAGGCTCC AACACATGCT TTAGCCGGGA AGCTTGAGGT       60

GGGGAAAAGC TGAGGCGGGC ACAGAGGAAG GTGTTGGGTG GCATCTGCGC TGTAGCCCGC      120

AGCCTGCGGC CCCAGCTCAT GTGTTTGTCA TTCTGTCTCC TCAGAGCGGG GCCATGGAGG      180

GGGAGACTCT TCACACATTC TACACTCAGC TGGTGTTGAT GCCCAAGGTG ATGCACTATG      240

CCCAGTACGT CCTCCTGGCG CTGGGCTGCG TCCTGCTGCT GGTCCCTGTC ATCTGCCAAA      300

TCCGGAGCCA AGTAGGTGCT GGCCAGAGGG CAGCCCGGGC TGACAGCCAT TCGCTTGCCT      360

GCTGGGGGAA AGGGGCCTCA GATCGGACCC TCTGGCCAAC CGCAGCCTGG AGCCCACCTC      420

CAGCAGCAGT CCTGCGTCTC TGCCGGAGTG GGAGCGGTCA CTGCTGGGGG              470

(2) INFORMATION FOR SEQ ID NO:16:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CCCCACATCT CAGCCACCTG CAATCGTTGA GGGTTGTTGG ACTCTAAACT TATGTGCCTT       60

TCCTGTTTCC TCTTTGCCTT TTGCAAATTG AAGAACCGTG TAAAACCATT TTTATGTGGC      120

TTCAACGTCA ACTATAAATT AGCTTGGTTA TCTTCTAGGA GAAATGCTAT TTATTTTGGA      180

GTAGTAGTAA AAAGGGCTCA AGGATAAGG AGGCCATTCA GGCCTATTCT GAATCCCTGA      240

TGACATCAGC TCCCAAGGGC TCTGTGCTGC AGGAAGCAAA ACTGTAGGTG GGTACCAGGT      300

AATGCCGTGC GCCTCCCCGC CCCCTCCCAT ATCAAGTAGA ATGCTGGCGG CTTAAAACAT      360

TTGGGGTCCT GCTCATTCCT TCAGCCTCAA CTTCACCTGG AGTGTCTACA GACTGAAGAT      420

GCATATTTGT GTATTTTGCT TTTGGAGAAA                                      450

(2) INFORMATION FOR SEQ ID NO:17:

(i) SEQUENCE CHARACTERISTICS:
        (A) LENGTH: 544 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

ACTGCGGAGA TGAGGGTCTA GAAGGTGGTG GCGGGGCATG TGGACCGTTG TAAGGGCTCT       60

GGGGTTCCTG GGTGGGCTGG CGAAGTCCTA CTCACAGTGA CCAACCATGA TGATGGTCCC      120

GATAGAGGAG GAGAGGGAGG AGGAGGGAAA AGGAAGGGTG AGGGGCTCAG AGGGGAGAGC      180
```

```
TGGGAGGAGG GGAGACATAG GTGGGGGAAG GGGTAGGAGA AAGGGGAAGG GAGCAAGAGG        240

GTGAGGGGCA CCAGGCCCCA TAGACGTTTT GGCTCAGCGG CCACGAGGCT TCATCAGCTC        300

CCGCCCCAAA ACGAAGCGA GGCCGTGGGG GCAGCGGCAG CATGGCGGGG CTTGTCTTGG         360

CGGCCATGGC CCCGCCCCCT GCCCGTCCGA TCAGCGCCCC GCCCCGTCCC CGCCCCGACC        420

CCGCCCCGGG CCCGCTCAGG CCCCGCCCCT GCCGCCGGAA TCCTGAAGCC CAAGGCTGCC        480

CGGGGGCGGT CCGGCGGCGC CGGCGATGGG GCATAAAACC ACTGGCCACC TGCCGGGCTG        540

CTCC                                                                    544

(2) INFORMATION FOR SEQ ID NO:18:

(i) SEQUENCE CHARACTERISTICS:
        (A) LENGTH: 190 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GTGGGTGAGG GAGACCCCAG GGGGTCCGCG CACGGACCCG GCTGTTGGG CGCTGGGCGC          60

CGGGAGGACC CGCGCGTTGC GGTGGGTGGG CGACCGCAGC GGAATCGGCG CCCGGGCCTG        120

GCGCCGCAGA ACACGAGGGA GGCCAGGCGC TTCGGGAGGG GCTGCTGCCC GCCTCCCCAC        180

CACCCTCACC                                                              190

(2) INFORMATION FOR SEQ ID NO:19:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

AGCCTCATGT GCGAAGGGCT TTCCCACCAC CTCCTATCCC AAGCTCCCGC CGAGGAGCCC         60

CTTCCCTGGC CGGGCTCGGG CAGCTGTTCC GGAGCCTTGT GGTGGGGCGT GGGGCCCTCA       120

TCACTCTCCT CACAAGCGTA CTTGTCCCTT CCCCTGCAG                              159

(2) INFORMATION FOR SEQ ID NO:20:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GTGAGGCTGT GTCCACGTGA TGGTGGACGG GCCGGCTGAC GCTGGGCATG GGACGGGTCT         60

CAAGTGGACG GGATGGGGAG GCTGCTGACT GACCCCAAA CATTGTTCCG GAAGCACGCA        120

ACTCATAGTC GGGGTAAGTG CTACTCCCAA AAAAGTTTGC GT                          162

(2) INFORMATION FOR SEQ ID NO:21:

(i) SEQUENCE CHARACTERISTICS:
        (A) LENGTH: 191 base pairs
        (B) TYPE: nucleic acid
```

```
        (C) STRANDEDNESS: single
        (D) TOPOLOGY: linear (ii) MOLECULE TYPE: DNA (genomic)

(xi) SEQUENCE DESCRIPTION: SEQ ID NO:21:

CATGTCCTGC AGTGGGCAGG CAGCGGGAGG GACAGACTTG GCGAAGGGGC CGAGCTCAGC        60

TTTGGCTGTG GGGCCGGAGG TGTGCACAGA CGTCCAGGGC CCCTGGTTCC CAGGCAGGCA       120

TTGCAGGCGA GTAGAAGGGA AACGTCCCAT GCAGCGGGGC GGGGCGTCTG ACCCACTGGC       180

TTCCCCCACA G                                                           191

(2) INFORMATION FOR SEQ ID NO:22:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GTGAGGCTGC CCTGTGGCCC ACGCCGCCTC GCACCCTGAC CTCGTCCCCT GTCTCTCCTC        60

CCGCCTGCCC CTTGTGCAGA GAGCAGTCCC TGAGGTGGTC GGAGCGTGGG GACTCACGCC       120

TGGTGGGTGG CTTTCGGCCC TGTGCTGTCT CCACCACCCC CA                         162

(2) INFORMATION FOR SEQ ID NO:23:

(i) SEQUENCE CHARACTERISTICS:
        (A) LENGTH: 161 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GGTGGTTCTG GTGTCCCAGA TGCCCCACGT GGCCACTCCA GGGGCCTCCT GCACCCCAGC        60

ATTTCCCTTC ATGGGCTCTT TGCTGTGAGG CCCAGCTGGG GCCAAGGGAG GATGGGCCAG       120

CCACGTCCAG CCTCTGACAC TAGTGTCCCT TCGCCTTGCA G                          161

(2) INFORMATION FOR SEQ ID NO:24:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GTACGTGTGG CCTGGTGAGA AGCCAAAGAT TCAGGCCTGT GTCCTGTCTT CCCCTCACAC        60

AGCCTGGACA CTGGTCACCA GCTTGCTTTG TAGCTGGCTG GGGATCTAGT GGCTGTGGGT       120

TGTAAGTGAC TGAGAACCTG ACTCAAACCG GCTTGAGTGA AA                         162

(2) INFORMATION FOR SEQ ID NO:25:

(i) SEQUENCE CHARACTERISTICS:
        (A) LENGTH: 160 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:25:

```
CCTCTCGGTC CCCAGACACT GGGCATTTGG CAGTGAACCA GATGCTGGGG GCCCTGTCCT      60
TCTGGTGGAG GGGGAGGAGG GCTCAGCCCA GAATGTTCAG ACCAGGCCGG CTCAATGGCA     120
GGCCTAAGCC TTACGATGCT GTTCCCTGCT GTGTCTGTAG                            160
```

(2) INFORMATION FOR SEQ ID NO:26:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

```
GTGAGGGGCG AGAGGCGAGG GCCCCTGTCG CCAGGGAGAG GGGAGGGTGG GCCCGGCCAT      60
GGCTGCTCGG GAGTGGCAGG GACCAGAGAG CTCCTTCTTC CTTTGTCGTG AAGAGGGTGC     120
TGGGAGGATG AACACTCTTG AAGTTGGAGG AGGGATTTTA                            160
```

(2) INFORMATION FOR SEQ ID NO:27:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

```
TCTCTGTGTG TCTACATAGC CTGCCCTCTT CCCACCGTGC CAGTATTGGG AATTGAGTGG      60
CCGTGCGTGC ACCAGGGTGA GTTAGGTGTG CAGCACCTGA GAGGGCTTAT TAAGGGGCCT     120
TGGCCCTACT GAGGGGTCTA GTCTGGATGC TTCCCCCCAG                            160
```

(2) INFORMATION FOR SEQ ID NO:28:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

```
GTAATCACTG GGACTCGGGG CCTCCTGGGT TTCCTGGGTA GCTCATGGCC AAATTCTGTG      60
GTGTTGGCTG TGCACTTGGA AAGCATTTTG ACTCATCGTG GATTTGACTC AGTAGCCCTT     120
GGCACCAGCT TGAATTCTCT TTGGTCACAC CACCAAAAGC                            160
```

(2) INFORMATION FOR SEQ ID NO:29:

(i) SEQUENCE CHARACTERISTICS:
        (A) LENGTH: 161 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

```
GGAGGTCGCT GCAGCTCCGC GGGTGAGAGA TGGGGGCGGT TTGGACCCGG GAGGTGGTAG          60

CGCCCGTGGG GAGAAGTGGC TGGATCTGGG CAGCCTTTGG CAGGGCCTGG CTCTGGCCGC         120

CGGGTCTGGG TGTCCCCTCT CATCCTGTCT GTCCCCTGCA G                            161

(2) INFORMATION FOR SEQ ID NO:30:

(i) SEQUENCE CHARACTERISTICS:
         (A) LENGTH: 153 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:30:

GTACGTGCCG TCCCCTGTTC TGGGATNGCC GGAGGGTGTT AGGTNTNGGG CACCTNANGG          60

TTTATCTGCC CAATGCTGTC TGCTTAATCT CTGGCCTCTG TACTCTTGAT AACCCATTAA         120

GCCAAAAATA TGATGCCTCT GGGACGATAT CTG                                     153

(2) INFORMATION FOR SEQ ID NO:31:

(i) SEQUENCE CHARACTERISTICS:
         (A) LENGTH: 162 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:31:

TGGGGCTTTT TACAGAATGG AGGAAGGGAT CCTCTCTGTC GGGTATTATG GTCATCGCCA          60

CGGGGGTGCC GTGCAGACCA CAGCTCTGTG CAGACTTCCG GAGTGGCAGG ACGTGCCAAT         120

ATACTGTCGT TGTATGATGT CCCCTCCCTG CCCTTGTTGT AG                           162

(2) INFORMATION FOR SEQ ID NO:32:

(i) SEQUENCE CHARACTERISTICS:
         (A) LENGTH: 149 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:32:

GTGAGCCCCT GCCATCCTCT GTGGGGGGTG GGTGATTCCT GGTTGGAGCA CACCTGGCTG          60

CCTCCTCTCT CCCCAGGCAG AGAGCTGCTG TGGGCTGGGG TGGTGGGAAG CCTGGCTTCT         120

AGAATCTCGA GCCACCAAAG TTCCTTACT                                          149

(2) INFORMATION FOR SEQ ID NO:33:

(i) SEQUENCE CHARACTERISTICS:
         (A) LENGTH: 157 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:33:

CCCCAGCCTG TGGCTTGTTT TAGGTAAGAT ACAAGCAAGC TCCACTGGGC AGTTAGCTGG          60

GACGCCCACC CTCTTGACTG GGACCAGGGA AAAGAAGGTT GACTGTGTCC CTGGAGCTTG         120
```

```
GGGGTGGCCA GTCTCCTCAC TGTGTTTGTT GCCGCAG                                    157
```

(2) INFORMATION FOR SEQ ID NO:34:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

```
GTGAGTGGGG ACTGGGAACT GGGGCTGCAT TGCTCATTGA GAGATTANGT GCTCAGTGCT           60

CCAGTGTTCC CAGACTCCCC TGACATACCC CAGGAAACAG GGCATGGGGA AGGGAGAGGG          120

TCCTATTGGG GGTGGAATCC AGTCCCTGCT GATCTTCTC                                 159
```

(2) INFORMATION FOR SEQ ID NO:35:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

```
ATGGCTCCTA AAGTGTTTCA GCTCATTGTT TATATTTGGT GGTGAGGGTT TAGTGTGTGC           60

AAAATTATAC TAAACCTGTT TAGATGTTGT ATTCAAGCAG AATTAGATCA AGTTTGGGTG          120

TAAGACTTTG TTCCAACACC TATGTCTTGC TTATTTCCAG                                160
```

(2) INFORMATION FOR SEQ ID NO:36:

(i) SEQUENCE CHARACTERISTICS:
        (A) LENGTH: 158 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

```
GTAAGGGTGC GTTGGGCACA GCGTCGGGGG CTTTTGTTAA TAGCCAATGT GGGCATTTGA           60

GGCAGGAGGC GGGGGGAGCA CCTTGTAGAA AGGGAGAGGG CTGAGCCAGG GTAACCGGAC          120

TGTTACATGG ACCAGCGTAT CATACACTTC ACCCTGTC                                  158
```

(2) INFORMATION FOR SEQ ID NO:37:

(i) SEQUENCE CHARACTERISTICS:
        (A) LENGTH: 164 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

```
CCTGGAGGGA GGAGGTCCCT GGCAGGCTCC AACACATGCT TTAGCCGGGA AGCTTGAGGT           60

GGGGAAAAGC TGAGGCGGGC ACAGAGGAAG GTGTTGGGTG GCATCTGCGC TGTAGCCCGC          120

AGCCTGCGGC CCCAGCTCAT GTGTTTGTCA TTCTGTCTCC TCAG                           164
```

(2) INFORMATION FOR SEQ ID NO:38:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

```
GTAGGTGCTG GCCAGAGGGC AGCCCGGGCT GACAGCCATT CGCTTGCCTG CTGGGGAAA        60

GGGGCCTCAG ATCGGACCCT CTGGCCAACC GCAGCCTGGA GCCCACCTCC AGCAGCAGTC      120

CTGCGTCTCT GCCGGAGTGG GAGCGGTCAC TGCTGGGGG                              159
```

(2) INFORMATION FOR SEQ ID NO:39:

(i) SEQUENCE CHARACTERISTICS:
        (A) LENGTH: 158 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

```
CCCCACATCT CAGCCACCTG CAATCGTTGA GGGTTGTTGG ACTCTAAACT TATGTGCCTT       60

TCCTGTTTCC TCTTTGCCTT TTGCAAATTG AAGAACCGTG TAAAACCATT TTTATGTGGC      120

TTCAACGTCA ACTATAAATT AGCTTGGTTA TCTTCTAG                              158
```

(2) INFORMATION FOR SEQ ID NO:40:

(i) SEQUENCE CHARACTERISTICS:
        (A) LENGTH: 163 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

```
GTGGGTACCA GGTAATGCCG TGCGCCTCCC CGCCCCCTCC CATATCAAGT AGAATGCTGG       60

CGGCTTAAAA CATTTGGGGT CCTGCTCATT CCTTCAGCCT CAACTTCACC TGGAGTGTCT      120

ACAGACTGAA GATGCATATT TGTGTATTTT GCTTTTGGAG AAA                        163
```

(2) INFORMATION FOR SEQ ID NO:41:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:41:

```
CCCCTGCCGC CGGAATCCTG AAG                                               23
```

(2) INFORMATION FOR SEQ ID NO:42:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
             (A) DESCRIPTION: /desc = "primer"

(xi) SEQUENCE DESCRIPTION: SEQ ID NO:42:

CGCTTTGGCG GAGCAGCCCA TGTC                                              24

(2) INFORMATION FOR SEQ ID NO:43:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(xi) SEQUENCE DESCRIPTION: SEQ ID NO:43:

TGGGGCCCTC ATCACTCTCC TCAC                                              24

(2) INFORMATION FOR SEQ ID NO:44:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(xi) SEQUENCE DESCRIPTION: SEQ ID NO:44:

GCAGCCTCCC CATCCCGTCC ACT                                               23

(2) INFORMATION FOR SEQ ID NO:45:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(xi) SEQUENCE DESCRIPTION: SEQ ID NO:45:

ATTGCAGGCG AGTAGAAG                                                     18

(2) INFORMATION FOR SEQ ID NO:46:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(xi) SEQUENCE DESCRIPTION: SEQ ID NO:46:

CAGGCGGGAG GAGAGACA                                                     18

(2) INFORMATION FOR SEQ ID NO:47:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
            (A) DESCRIPTION: /desc = "primer"

(xi) SEQUENCE DESCRIPTION: SEQ ID NO:47:

TGGGCTCTTT GCTGTGAGGC                                                    20

(2) INFORMATION FOR SEQ ID NO:48:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:48:

CCAGGCTGTG TGAGGGGAAG                                                    20

(2) INFORMATION FOR SEQ ID NO:49:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:49:

GCCCAGAATG TTCAGACCAG                                                    20

(2) INFORMATION FOR SEQ ID NO:50:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:50:

GCACCCTCTT CACGACAAAG                                                    20

(2) INFORMATION FOR SEQ ID NO:51:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:51:

CACCTGAGAG GGCTTATTA                                                     19

(2) INFORMATION FOR SEQ ID NO:52:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
        (A) DESCRIPTION: /desc = "primer"

(xi) SEQUENCE DESCRIPTION: SEQ ID NO:52:

CAAAATGCTT TCCAAGTGC                                            19

(2) INFORMATION FOR SEQ ID NO:53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:53:

GCCGCCGGGT CTGGGTGTCC                                           20

(2) INFORMATION FOR SEQ ID NO:54:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:54:

CAGAGGCCAG AGATTAAGCA GAC                                       23

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:55:

TTGTATGATG TCCCCTCCCT                                           20

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:56:

TTCCCACCAC CCCAGCCCAC                                           20

(2) INFORMATION FOR SEQ ID NO:57:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "primer"

(xi) SEQUENCE DESCRIPTION: SEQ ID NO:57:

GGTTGACTGT GTCCCTGGAG                                                           20

(2) INFORMATION FOR SEQ ID NO:58:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:58:

GGGAACACTG GAGCACTGAG C                                                         21

(2) INFORMATION FOR SEQ ID NO:59:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:59:

GGTGGTGAGG GTTTAGTGTG                                                           20

(2) INFORMATION FOR SEQ ID NO:60:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:60:

CTCCCCCCGC CTCCTGCCTC                                                           20

(2) INFORMATION FOR SEQ ID NO:61:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:61:

AAGGTGTTGG GTGGCATCTG                                                           20

(2) INFORMATION FOR SEQ ID NO:62:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
        (A) DESCRIPTION: /desc = "primer"

(xi) SEQUENCE DESCRIPTION: SEQ ID NO:62:

GGCTCCAGGC TGCGGTTGGC                                                   20

(2) INFORMATION FOR SEQ ID NO:63:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:63:

TTGAAGAACC GTGTAAAAC                                                    19

(2) INFORMATION FOR SEQ ID NO:64:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:64:

TTGAGGCTGA AGGAATGA                                                     18

(2) INFORMATION FOR SEQ ID NO:65:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

GTGAGGGGCG AGAGGCGAGG GCCCCTGTCG CCAGGGAGAG GGGAGGGTGG GCCTGGCCAT        60

GGCTGCTCGG GAGTGGCAGG GACCAGAGAG CTCCTTCTTC CTTTGTCGTG AAGAGGGTGC      120

TGGGAGGATG AACACTCTTG AAGTTGGAGG AGGGATTTTA                            160

(2) INFORMATION FOR SEQ ID NO:66:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:66:

AGCCATGGCC GGGCCCACCC T                                                 21

(2) INFORMATION FOR SEQ ID NO:67:

(i) SEQUENCE CHARACTERISTICS:
        (A) LENGTH: 31 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:67:

CGAGCAGCCA TGGCCGGGCC CACCCTCCCC T                            31

(2) INFORMATION FOR SEQ ID NO:68:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:68:

AGGGTGGGCC CGGCCATGGC T                                      21

(2) INFORMATION FOR SEQ ID NO:69:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:69:

AGGGGAGGGT GGGCCCGGCC ATGGCTGCTC G                            31

(2) INFORMATION FOR SEQ ID NO:70:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:70:

AGCCATGGCC AGGCCCACCC T                                      21

(2) INFORMATION FOR SEQ ID NO:71:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:71:

CGAGCAGCCA TGGCCAGGCC CACCCTCCCC T                            31

(2) INFORMATION FOR SEQ ID NO:72:

(i) SEQUENCE CHARACTERISTICS:
        (A) LENGTH: 21 base pairs

```
            (B) TYPE: nucleic acid
            (C) STRANDEDNESS: single
            (D) TOPOLOGY: linear (ii) MOLECULE TYPE: other nucleic acid
            (A) DESCRIPTION: /desc = "probe"

(xi) SEQUENCE DESCRIPTION: SEQ ID NO:72:

AGGGTGGGCC TGGCCATGGC T                                              21

(2) INFORMATION FOR SEQ ID NO:73:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "probe"

(xi) SEQUENCE DESCRIPTION: SEQ ID NO:73:

AGGGGAGGGT GGGCCTGGCC ATGGCTGCTC G                                   31

(2) INFORMATION FOR SEQ ID NO:74:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:74:

TGTAAAACGA CGGCCAGT                                                  18

(2) INFORMATION FOR SEQ ID NO:75:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:75:

CAGGAAACAG CTATGACC                                                  18
```